(12) United States Patent
Hirokawa

(10) Patent No.: US 12,327,347 B2
(45) Date of Patent: Jun. 10, 2025

(54) IMAGE PROCESSING METHOD, IMAGE PROCESSING DEVICE, AND STORAGE MEDIUM

(71) Applicant: NIKON CORPORATION, Tokyo (JP)

(72) Inventor: Mariko Hirokawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 17/474,288

(22) Filed: Sep. 14, 2021

(65) Prior Publication Data

US 2021/0407087 A1 Dec. 30, 2021

Related U.S. Application Data

(63) Continuation of application No. 16/669,119, filed on Oct. 30, 2019, now Pat. No. 11,151,718.

(51) Int. Cl.
| | |
|---|---|
| *G06T 7/00* | (2017.01) |
| *A61B 3/12* | (2006.01) |
| *A61B 5/02* | (2006.01) |
| *A61B 5/107* | (2006.01) |
| *G06T 7/62* | (2017.01) |
| *G06T 7/66* | (2017.01) |

(52) U.S. Cl.
CPC .............. *G06T 7/0012* (2013.01); *A61B 3/12* (2013.01); *A61B 5/02007* (2013.01); *A61B 5/1075* (2013.01); *G06T 7/62* (2017.01); *G06T 7/66* (2017.01); *G06T 2207/30041* (2013.01); *G06T 2207/30101* (2013.01)

(58) Field of Classification Search
CPC ... A61B 2576/02; A61B 3/102; A61B 3/1025; A61B 3/12; A61B 5/02007; A61B 5/1075; A61B 5/489; G06T 2207/10101; G06T 2207/30041; G06T 2207/30101; G06T 7/0012; G06T 7/11; G06T 7/136; G06T 7/62; G06T 7/66
See application file for complete search history.

(56) References Cited

U.S. PATENT DOCUMENTS

| | | | |
|---|---|---|---|
| 2004/0249270 A1 | 12/2004 | Kondo et al. | |
| 2014/0073917 A1 | 3/2014 | Huang et al. | |
| 2015/0164478 A1* | 6/2015 | Jung ................... | G01S 7/52063 |
| | | | 600/443 |

(Continued)

FOREIGN PATENT DOCUMENTS

| | | |
|---|---|---|
| JP | 2004-283373 A | 10/2004 |
| JP | 2007-097740 A | 4/2007 |

(Continued)

OTHER PUBLICATIONS

Japanese Office Action for Japan Application No. 2018-192118 issued on May 10, 2022.

(Continued)

*Primary Examiner* — Manuchehr Rahmjoo
(74) *Attorney, Agent, or Firm* — Foley & Lardner LLP

(57) ABSTRACT

An image processing method, which is executed by a processor, comprises acquiring a choroidal vascular image, identifying, in the choroidal vascular image, a plurality of blood vessel center points of a choroidal blood vessel along a flow direction of the choroidal blood vessel, and computing a blood vessel diameter for each of the plurality of identified blood vessel center points.

8 Claims, 31 Drawing Sheets

(56) References Cited

U.S. PATENT DOCUMENTS

2016/0135683 A1    5/2016    Yasuno et al.
2016/0310101 A1*   10/2016    Lee ..................... A61B 8/4427
2017/0112377 A1    4/2017    Shiba et al.
2019/0274538 A1    9/2019    Imamura et al.

FOREIGN PATENT DOCUMENTS

JP      2016-043155 A    4/2016
JP      2017-077414 A    4/2017

OTHER PUBLICATIONS

Japanese Office Action in corresponding Japanese Application No. 2023-031413, dated Nov. 7, 2023 (6 pages).

* cited by examiner

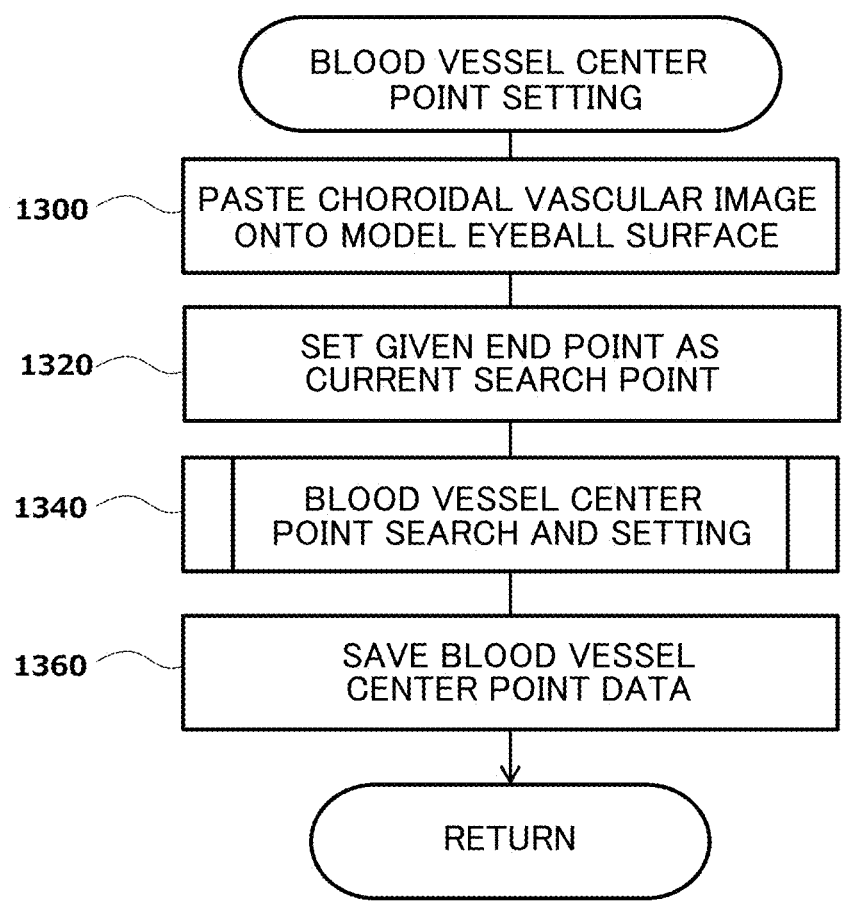

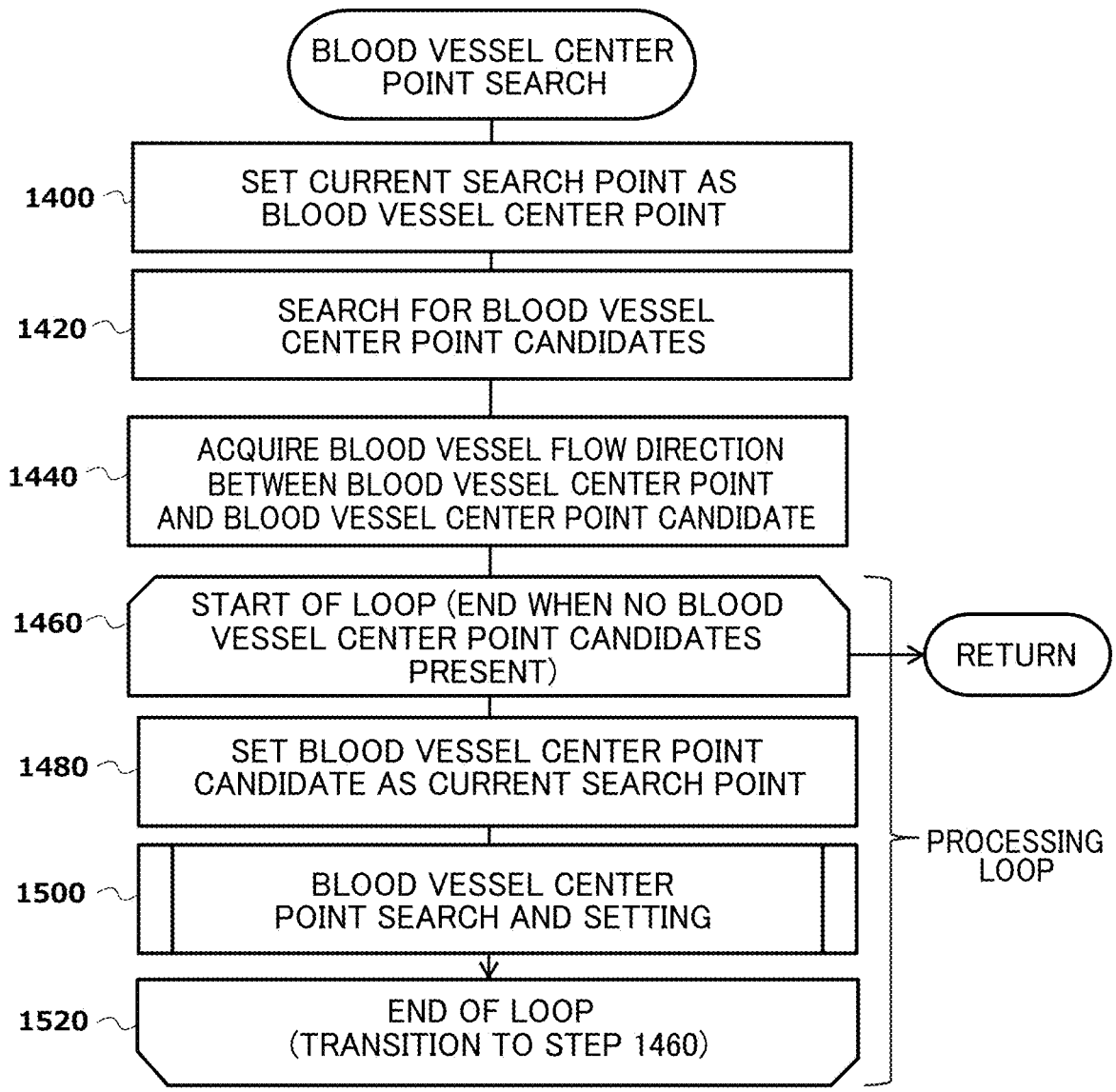

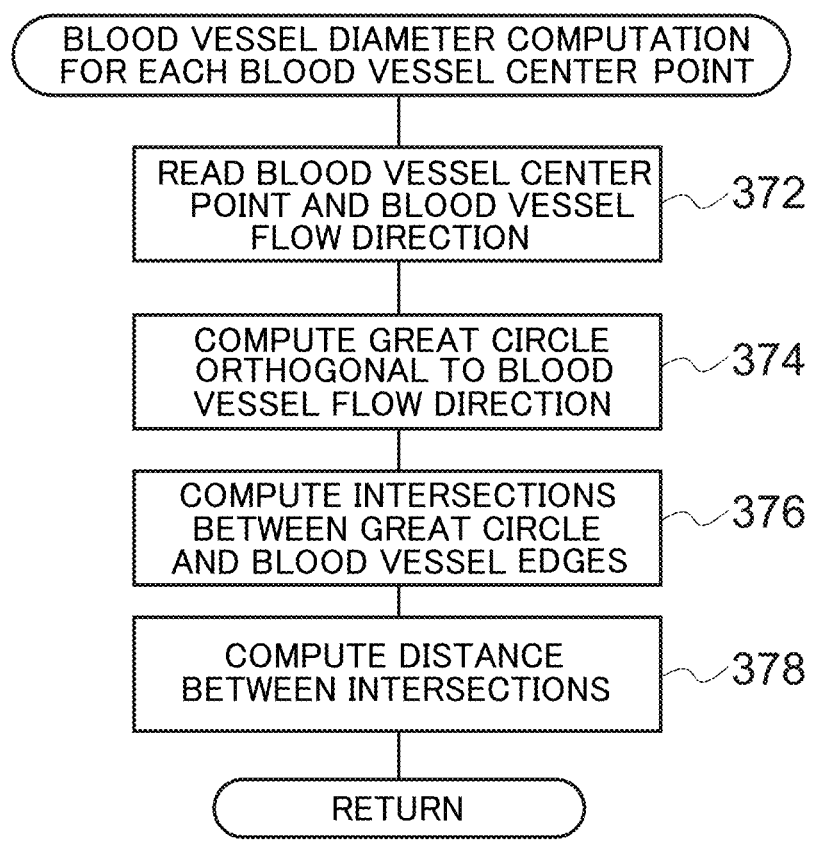

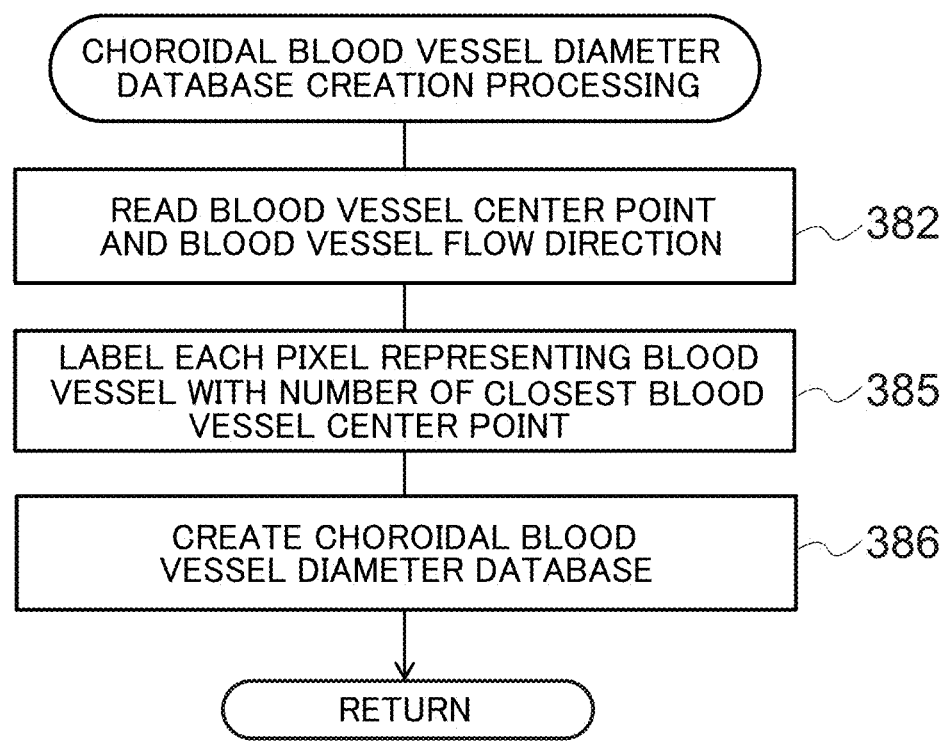

VASCULAR NETWORK GRAPH

FIG.26

| 502 | 504 | 506 | 508 | 510 | 512 | 514 | 516 | 518 |
|---|---|---|---|---|---|---|---|---|
| DATA # | SKELETON # | BLOOD VESSEL LENGTH | TOTAL COUNT OF BLOOD VESSEL CENTER POINTS | BLOOD VESSEL CENTER POINT # | COORDINATES OF BLOOD VESSEL CENTER POINT IN SLO IMAGE | COORDINATES OF PIXELS APPENDED WITH BLOOD VESSEL CENTER POINT # | BLOOD VESSEL FLOW DIRECTION | BLOOD VESSEL DIAMETER |
| CHOROIDAL VASCULAR IMAGE 1 | S1 | LS1 | NS1 | #1 | (x1, y1) | G11(x11,y11) G12(x12,y12) G13(x13,y13) ... | θ #1 | r #1 |
|  |  |  |  | #2 | (x2, y2) | G21(x21,y21) G22(x22,y22) G23(x23,y23) ... | θ #2 | r #2 |
|  |  |  |  | ... |  |  |  |  |
|  | S2 | LS2 | NS2 |  |  |  |  |  |
|  | ... | ... | ... |  |  |  |  |  |
| CHOROIDAL VASCULAR IMAGE 2 |  |  |  |  |  |  |  |  |

FIG.27

| 502 | 504 | 506 | 508 | 510 | 512 | 518 |
|---|---|---|---|---|---|---|
| DATA # | SKELETON # | BLOOD VESSEL LENGTH | TOTAL COUNT OF BLOOD VESSEL CENTER POINTS | BLOOD VESSEL CENTER POINT # | COORDINATES OF BLOOD VESSEL CENTER POINT IN SLO IMAGE | BLOOD VESSEL DIAMETER |
| | | | | | | |

| 514 | 516 |
|---|---|
| COORDINATES OF PIXELS APPENDED WITH BLOOD VESSEL CENTER POINT # | BLOOD VESSEL FLOW DIRECTION |
| | |

US 12,327,347 B2

IMAGE PROCESSING METHOD, IMAGE PROCESSING DEVICE, AND STORAGE MEDIUM

CROSS-REFERENCE TO RELATED APPLICATION

The present application is a continuation of U.S. patent application Ser. No. 16/669,119, filed on Oct. 30, 2019, which is based on Japanese Patent Application No. 2018-192118 filed on Oct. 10, 2018. The entire contents of all of the above applications are incorporated by reference herein entirely.

BACKGROUND

Technical Field

Technology disclosed herein relates to an image processing method, an image processing device, and a storage medium.

Related Art

The specification of US Patent Application Laid-Open No. 2016/0135683A1 discloses visualizing a network of choroidal blood vessels. There has been a desire hitherto to obtain the diameters of blood vessels in the choroid.

SUMMARY

A first aspect of the present disclosure is an image processing method executed by a processor, the image processing method comprising acquiring a choroidal vascular image, identifying, in the choroidal vascular image, a plurality of blood vessel center points of a choroidal blood vessel along a flow direction of the choroidal blood vessel, and computing a blood vessel diameter for each of the plurality of identified blood vessel center points.

A second aspect of the present disclosure is an image processing device comprising memory and a processor coupled to the memory, wherein the processor is configured to acquire a choroidal vascular image, identify, in the choroidal vascular image, a plurality of blood vessel center points of a choroidal blood vessel along a flow direction of the choroidal blood vessel, and compute a blood vessel diameter for each of the plurality of identified blood vessel center points.

A third aspect of the present disclosure is a storage medium being not a transitory signal and stored with an image processing program that causes a computer to execute processing, the processing comprising acquiring a choroidal vascular image, identifying, in the choroidal vascular image, a plurality of blood vessel center points of a choroidal blood vessel along a flow direction of the choroidal blood vessel, and computing a blood vessel diameter for each of the plurality of identified blood vessel center points.

BRIEF DESCRIPTION OF THE DRAWINGS

Exemplary embodiments of the present disclosure will be described in detail based on the following figures, wherein:

FIG. 9A is a flowchart of processing performed at step 324 in FIG. 7;

FIG. 9B is a flowchart of a blood vessel center point search subroutine performed at step 1340 in FIG. 9A;

FIG. 10 is a flowchart of processing performed at step 326 in FIG. 7;

FIG. 11 is a flowchart of choroidal blood vessel diameter database creation processing performed at step 309 in FIG. 6;

FIG. 26 is a diagram illustrating a database of choroidal blood vessel diameters;

FIG. 27 is a diagram illustrating another database of choroidal blood vessel diameters;

DETAILED DESCRIPTION

Detailed explanation follows regarding exemplary embodiments of technology disclosed herein, with reference to the drawings.

First Exemplary Embodiment

Explanation follows regarding a model eyeball according to a first exemplary embodiment of technology disclosed herein, with reference to the drawings.

Figure 1:
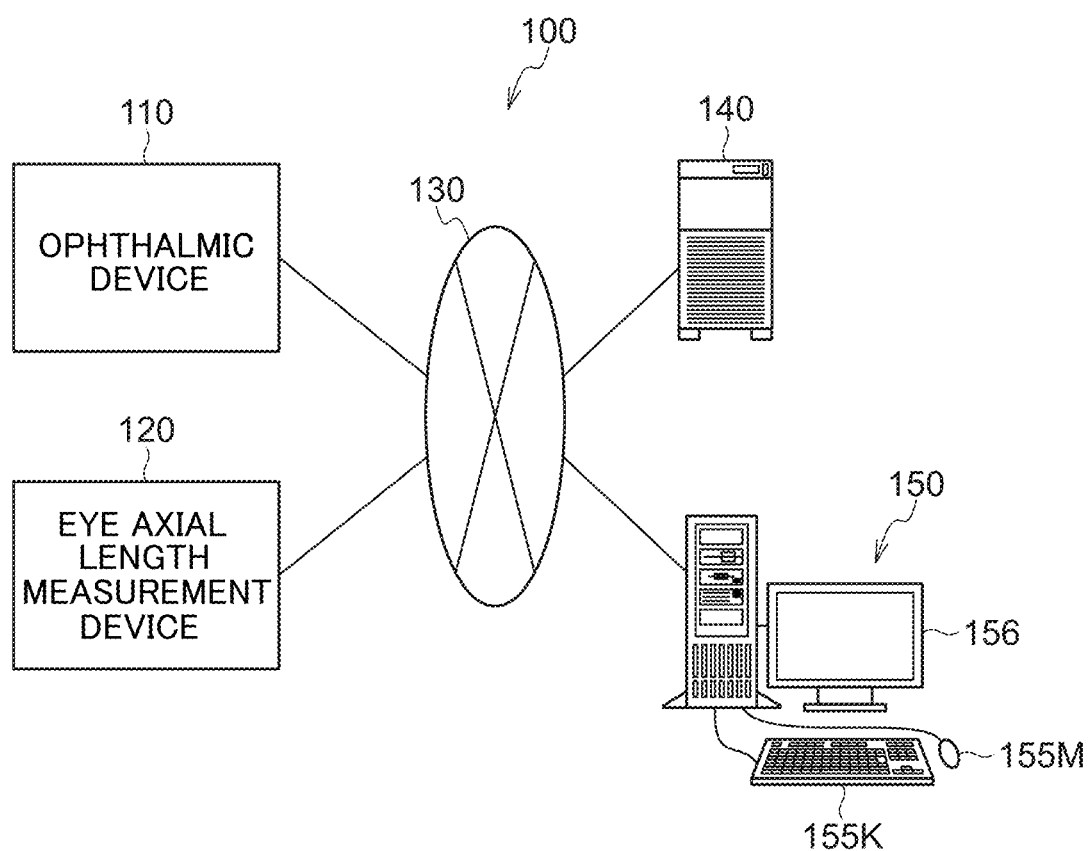
FIG. 1 is a block diagram of an ophthalmic system 100.

Configuration of an ophthalmic system 100 will now be explained with reference to FIG. 1. As illustrated in FIG. 1, the ophthalmic system 100 includes an ophthalmic device 110, an eye axial length measurement device 120, a management server device (referred to hereafter as "management server") 140, and an image display device (referred to hereafter as "image viewer") 150. The ophthalmic device 110 acquires an image of the fundus. The eye axial length measurement device 120 measures the axial length of the eye of a patient. The management server 140 stores plural fundus images, eye axial lengths, and tomographic images obtained by imaging the fundus of plural patients using the ophthalmic device 110, and stores these in association with patient IDs. The image viewer 150 displays fundus images acquired from the management server 140.

The management server 140 is an example of an "image processing device" and of a "blood vessel diameter computation device" of technology disclosed herein.

The ophthalmic device 110, the eye axial length measurement device 120, the management server 140, and the image viewer 150 are coupled together over a network 130.

The eye axial length measurement device 120 has two modes for measuring eye axial length, this being the length of an examined eye 12 in an eye axial direction: a first mode and a second mode. In the first mode, after light from a non-illustrated light source is guided into the examined eye 12, interference between light reflected from the fundus and light reflected from the cornea is photo-detected as interference light, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the management server 140. The eye axial length may be measured using both the first mode and the second mode, and in such cases, an average of the eye axial lengths as measured using the two modes is transmitted to the management server 140 as the eye axial length.

Figure 2:
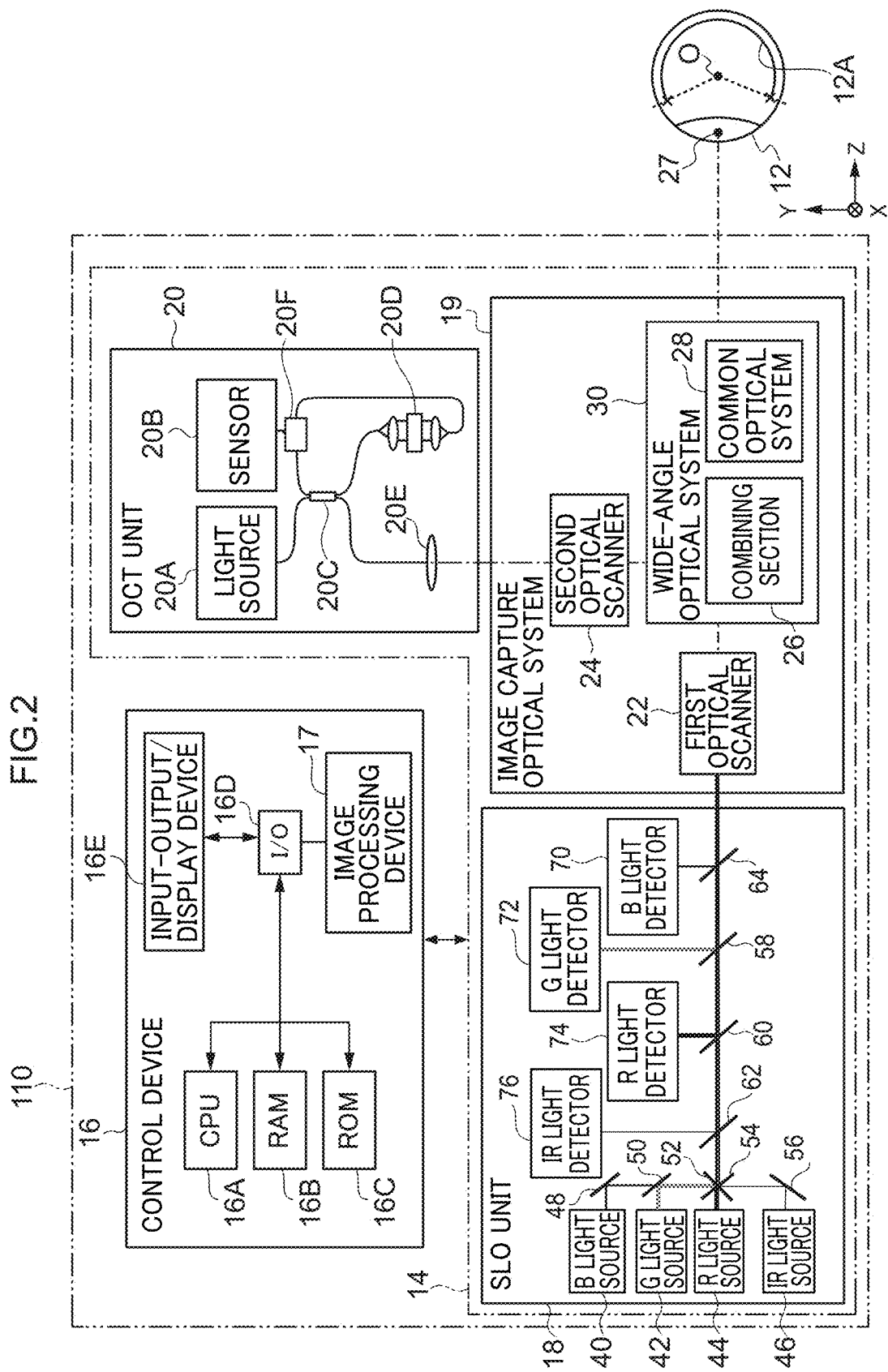
FIG. 2 is a schematic configuration diagram illustrating an overall configuration of an ophthalmic device 110.

Explanation follows regarding configuration of the ophthalmic device 110, with reference to FIG. 2.

For ease of explanation, scanning laser ophthalmoscope is abbreviated to SLO, and optical coherence tomography is abbreviated to OCT.

In cases in which the ophthalmic device 110 is installed on a horizontal plane with a horizontal direction taken as an X direction, a direction perpendicular to the horizontal plane is denoted as being a Y direction, and a direction connecting the center of the pupil at the anterior segment of the examined eye 12 and the center of the eyeball is denoted as being a Z direction. The X direction, the Y direction, and the Z direction are thus mutually perpendicular directions.

The ophthalmic device 110 includes an imaging device 14 and a control device 16. The imaging device 14 is provided with an SLO unit 18 and an OCT unit 20, and acquires a fundus image of the fundus of the examined eye 12. Two-dimensional fundus images that have been acquired by the SLO unit 18 are referred to hereafter as SLO images. Tomographic images, face-on images (en-face images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input-output/display device 16E coupled to the CPU 16A through the I/O port 16D. The input-output/display device 16E includes a graphical user interface to display images of the examined eye 12 and to receive various instructions from a user. An example of the graphical user interface is a touch panel display.

The control device 16 is provided with an image processing device 17 coupled to the I/O port 16D. The image processing device 17 generates images of the examined eye 12 based on data acquired by the imaging device 14. Note that the control device 16 is coupled to the network 130 through a communication interface, not illustrated in the drawings.

Although the control device 16 of the ophthalmic device 110 is provided with the input-output/display device 16E as illustrated above in FIG. 2, the technology disclosed herein is not limited thereto. For example, a configuration may adopted in which the control device 16 of the ophthalmic device 110 is not provided with the input-output/display device 16E, and instead a separate input-output/display device is provided that is physically independent of the ophthalmic device 110. In such cases, the display device is provided with an image processing processor unit that operates under the control of a display control section 204 of the CPU 16A in the control device 16. Such an image processing processor unit may display SLO images and the like based on an image signal output as an instruction by the display control section 204.

The imaging device 14 operates under the control of an imaging control section 202 of the control device 16. The imaging device 14 includes the SLO unit 18, an image capture optical system 19, and the OCT unit 20. The image capture optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of polarizing light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refractive optical system employing a wide-angle lens, or may be a reflection-refractive optical system employing a combination of a concave mirror and a lens. Employing a wide-angle optical system that utilizes an elliptical minor, wide-angle lens, or the like enables imaging to be performed of not only a central portion of the fundus, but also of the retina at the periphery of the fundus.

For a system including an elliptical minor, a configuration may be adopted that utilizes an elliptical mirror system as disclosed in International Publication (WO) Nos. 2016/103484 or 2016/103489. The disclosures of WO Nos. 2016/103484 or 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with respect to a pupil 27. The internal illumination angle is the angle of illumination of a light beam shone onto the fundus F, and is an angle of illumination defined with respect to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

SLO fundus images obtained by imaging at an imaging angle having an internal illumination angle of 160° or greater are referred to as UWF-SLO fundus images. UWF is an abbreviation of ultra wide field.

An SLO system is realized by the control device 16, the SLO unit 18, and the image capture optical system 19 as illustrated in FIG. 2. The SLO system is provided with the wide-angle optical system 30, enabling fundus imaging over the wide FOV 12A.

The SLO unit 18 is provided with a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using transmission or reflection. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 52, 56. The respective lights are thereby guided onto a single optical path.

The SLO unit 18 is configured so as to be capable of switching between the light source or the combination of light sources employed for emitting laser light of different wavelengths, such as a mode in which R light and G light are emitted, a mode in which infrared light is emitted, etc. Although the example in FIG. 2 includes three light sources, i.e. the G light source 42, the R light source 44, and the IR light source 46, the technology disclosed herein is not limited thereto. For example, the SLO unit 18 may, furthermore, also include a blue (B) light source or a white light source, in a configuration in which light is emitted in various modes, such as a mode in which G light, R light, and B light are emitted or a mode in which white light is emitted alone.

Light introduced to the image capture optical system 19 from the SLO unit 18 is scanned in the X direction and the Y direction by the first optical scanner 22. The scanning light passes through the wide-angle optical system 30 and the pupil 27 and is shone onto the fundus. Reflected light that has been reflected by the fundus passes through the wide-angle optical system 30 and the first optical scanner 22 and is introduced into the SLO unit 18.

The SLO unit 18 is provided with a beam splitter 64 and a beam splitter 58. From out of the light coming from the posterior segment (fundus) of the examined eye 12, the B light therein is reflected by the beam splitter 64 and light other than B light therein is transmitted by the beam splitter 64. From out of the light transmitted by the beam splitter 64, the G light therein is reflected by the beam splitter 58 and light other than G light therein is transmitted by the beam splitter 58. The SLO unit 18 is further provided with a beam splitter 60 that, from out of the light transmitted through the beam splitter 58, reflects R light therein and transmits light other than R light therein. The SLO unit 18 is provided with a beam splitter 62 that reflects IR light from out of the light transmitted through the beam splitter 60. The SLO unit 18 is provided with a B light detector 70 to detect B light reflected by the beam splitter 64, a G light detector 72 to detect G light reflected by the beam splitter 58, an R light detector 74 to detect R light reflected by the beam splitter 60, and an IR light detector 76 to detect IR light reflected by the beam splitter 62.

Light that has passed through the wide-angle optical system 30 and the first optical scanner 22 and been introduced into the SLO unit 18 (i.e. reflected light that has been reflected by the fundus) is reflected by the beam splitter 64 and photo-detected by the B light detector 70 when B light, and is reflected by the beam splitter 58 and photo-detected by the G light detector 72 when G light. When R light, the incident light is transmitted through the beam splitter 58, reflected by the beam splitter 60, and photo-detected by the R light detector 74. When IR light, the incident light is transmitted through the beam splitters 58, 60, reflected by the beam splitter 62, and photo-detected by the IR light detector 76. The image processing device 17 that operates under the control of the CPU 16A employs signals detected by the B light detector 70, the G light detector 72, the R light detector 74, and the IR light detector 76 to generate UWF-SLO images.

Figure 12:
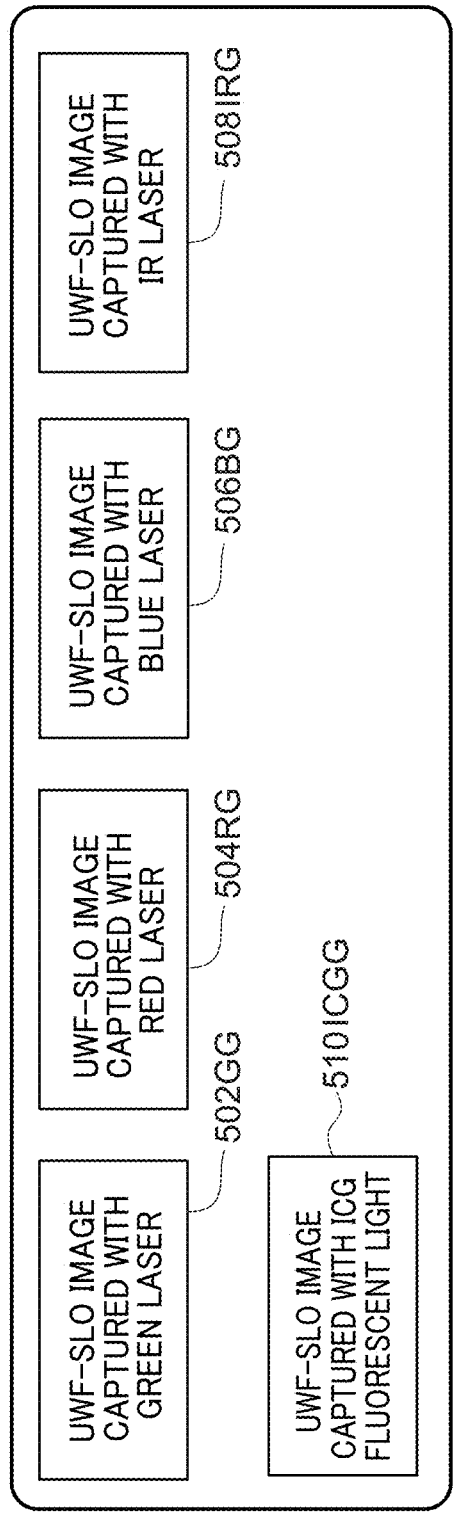
FIG. 12 is a diagram illustrating various UWF-SLO images obtained by an ophthalmic device 110.

As illustrated in FIG. 12, the UWF-SLO images include a UWF-SLO image (green fundus image) 502GG obtained by imaging the fundus in green, and a UWF-SLO image (red fundus image) 504RG obtained by imaging the fundus in red. The UWF-SLO images further include a UWF-SLO image (blue fundus image) 506BG obtained by imaging the fundus in blue, and a UWF-SLO image (IR fundus image) 508IRG obtained by imaging the fundus in IR.

The control device 16 may control the light sources 40, 42, 44 so as to emit light at the same time as each other. The green fundus image 502GG, the red fundus image 504RG, and the blue fundus image 506BG may be obtained at mutually corresponding each position by imaging the fundus of the examined eye 12 using B light, G light, and R light at the same time. An RGB color fundus image may be obtained from the green fundus image 502GG, the red fundus image 504RG, and the blue fundus image 506BG. The control device 16 may also control the light sources 42, 44 so as to emit light at the same time as each other. The green fundus image 502GG and the red fundus image 504RG are obtained at mutually corresponding positions by imaging the fundus of the examined eye 12 using G light and R light at the same time in this manner. An RG color fundus image may be obtained from the green fundus image 502GG and the red fundus image 504RG.

The UWF-SLO images further include an UWF-SLO image (video) 510ICGG imaged using ICG fluorescent light. When indocyanine green (ICG) is injected into a blood vessel so as to reach the fundus, the indocyanine green (ICG) first reaches the retina, then reaches the choroid, before passing through the choroid. The UWF-SLO image (video) 510ICGG is a video image from the time the indocyanine green (ICG) injected into a blood vessel reached the retina until after the indocyanine green (ICG) has passed through the choroid.

Each image data for the blue fundus image 506BG, the green fundus image 502GG, the red fundus image 504RG, the IR fundus image 508IRG, the RGB color fundus image, the RG color fundus image, and the UWF-SLO image 510ICGG are sent from the ophthalmic device 110 to the management server 140 through a non-illustrated communication IF.

An OCT system is realized by the control device 16, the OCT unit 20, and the image capture optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the image capture optical system 19. The measurement light is scanned in the X direction and the Y direction by the second optical scanner 24. The scanned light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processing device 17 operating under the control of an image processing control section 206 generates OCT images, such as tomographic images and en-face images, based on OCT data detected by the sensor 20B.

OCT fundus images obtained by imaging at an imaging angle having an internal illumination angle of 160° or greater are referred to as UWF-OCT images.

Image data of the UWF-OCT images is sent from the ophthalmic device 110 to the management server 140 through the non-illustrated communication IF and stored in a storage device 254.

Note that although in the present exemplary embodiment an example is given in which the light source 20A is a swept-source OCT (SS-OCT), the light source 20A may be from various OCT systems, such as from of a spectral-domain OCT (SD-OCT) or a time-domain OCT (TD-OCT) system.

The eye axial length measurement device 120 in FIG. 1 includes the two modes for measuring the examined eye axial length, this being the length of the examined eye 12 in the eye axial direction (Z direction): the first mode and the second mode. In the first mode, after light from a non-illustrated light source has been guided into the examined eye 12, light arising from interference between the reflected light from the fundus and the reflected light from the cornea is photo-detected, and the eye axial length is measured based on an interference signal as expressed by the photo-detected interference light. The second mode is a mode in which the eye axial length is measured using ultrasound waves, not illustrated in the drawings. The eye axial length measurement device 120 transmits the eye axial length as measured using the first mode or the second mode to the management server 140. The eye axial length may be measured using both the first mode and the second mode, and in such cases an average of the eye axial length as measured using the two modes is transmitted as the eye axial length to the management server 140. The eye axial length is one type of data about a subject, and the eye axial length is saved as patient information in the management server 140 as well as being utilized in fundus image analysis.

Figure 3:
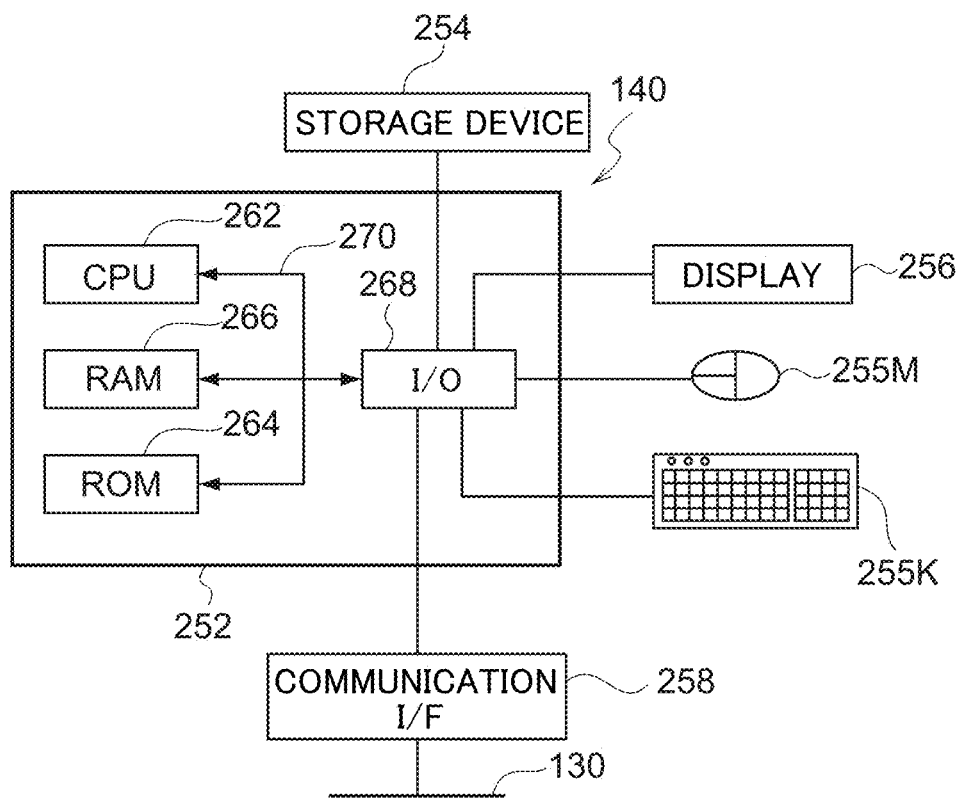
FIG. 3 is a block diagram of configuration of an electrical system of a management server 140.
Figure 4:
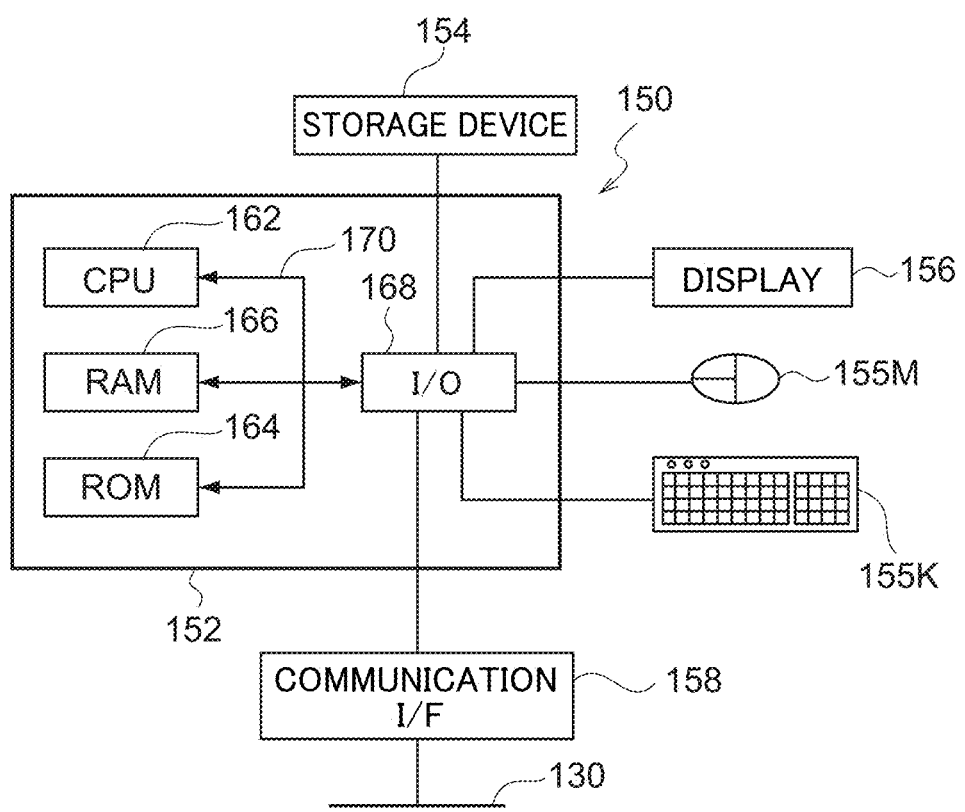
FIG. 4 is a block diagram illustrating a configuration of an electrical system of an image viewer 150.

Explanation follows regarding a configuration of an electrical system of the management server 140, with reference to FIG. 3. As illustrated in FIG. 4, the management server 140 is provided with a computer body 252. The computer body 252 includes a CPU 262, RAM 266, ROM 264, and an input/output (I/O) port 268. A storage device 254, a display 256, a mouse 255M, a keyboard 255K, and a communication interface (I/F) 258 are coupled to the input/output (I/O) port 268. The storage device 254 is, for example, configured by non-volatile memory. The input/output (I/O) port 268 is coupled to the network 130 through the communication interface (I/F) 258. The management server 140 is thus capable of communicating with the ophthalmic device 110, the eye axial length measurement device 120, and the image viewer 150. The storage device 254 is stored with an image processing program, described later. Note that the image processing program may be stored in the ROM 264.

The storage device 254 and the ROM 264 are each an example of a "storage medium" of the technology disclosed herein.

The management server 140 stores each data received from the ophthalmic device 110 and the eye axial length measurement device 120 in the storage device 254.

Explanation follows regarding a configuration of an electrical system of the image viewer 150, with reference to FIG. 4. As illustrated in FIG. 4, the image viewer 150 is provided with a computer body 152. The computer body 152 includes a CPU 162, RAM 166, ROM 164, and an input/output (I/O) port 168. A storage device 154, a display 156, a mouse 155M, a keyboard 155K, and a communication interface (I/F) 158 are coupled to the input/output (I/O) port 168. The storage device 154 is, for example, configured by non-volatile memory. The input/output (I/O) port 168 is coupled to the network 130 through the communication interface (I/F) 158. The image viewer 150 is thus capable of communicating with the ophthalmic device 110 and the management server 140.

Figure 5:
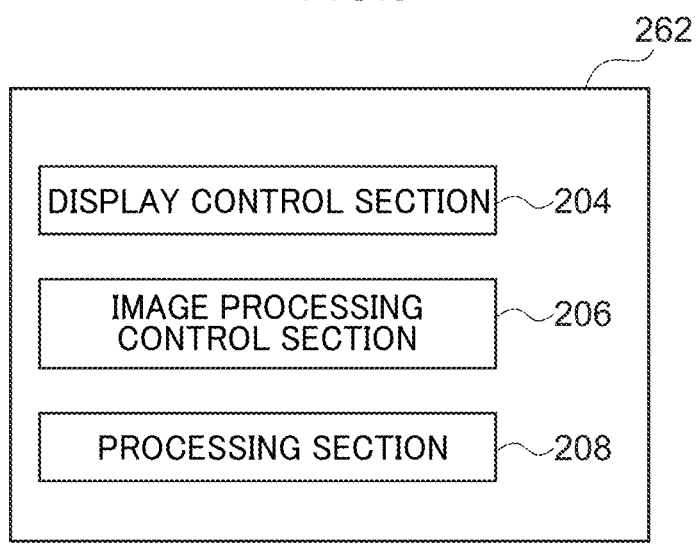
FIG. 5 is a block diagram illustrating functionality of a CPU 262 of a management server 140.

Explanation follows regarding various functions implemented by the CPU 262 of the management server 140 executing the image processing program, with reference to FIG. 5. The image processing program includes a display control function, an image processing control function, and a processing function. The CPU 262 functions as the display control section 204, the image processing control section 206, and a processing section 208, as illustrated in FIG. 6 by the CPU 262 executing the image processing program that includes these functions.

The image processing control section 206 is an example of a "choroidal vascular image acquisition section", an "identification section", a "computation section", a "storage processor", a "first identification section", a "second identification section", and a "control section".

Figure 6:
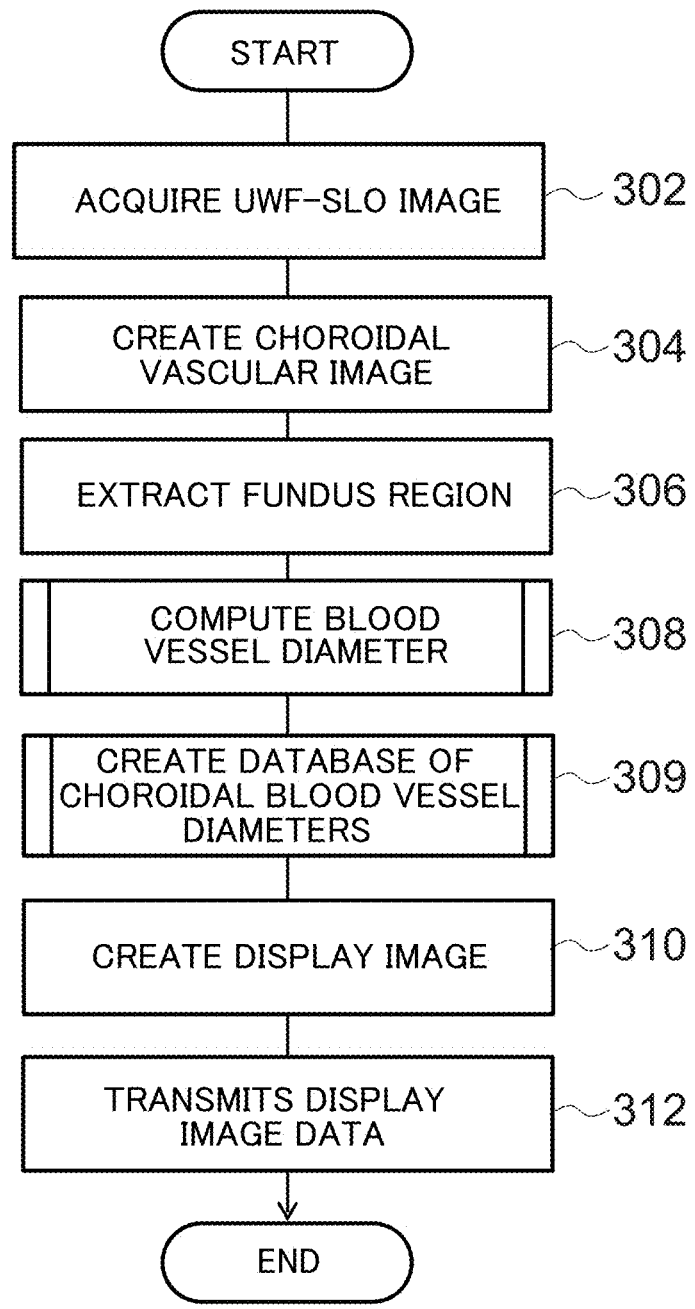
FIG. 6 is a flowchart of an image processing program.

Detailed explanation follows regarding image processing performed by the management server 140, with reference to FIG. 6. The image processing (image processing method) illustrated in the flowchart of FIG. 6 is realized by the CPU 262 of the management server 140 executing the image processing program.

At step 302, the image processing control section 206 acquires a UWF-SLO image from the storage device 254. At step 304, the image processing control section 206 creates a vascular image of the choroid from the acquired UWF-SLO image in the following manner.

First explanation follows regarding information contained in the red fundus image and the green fundus image.

Figure 13:
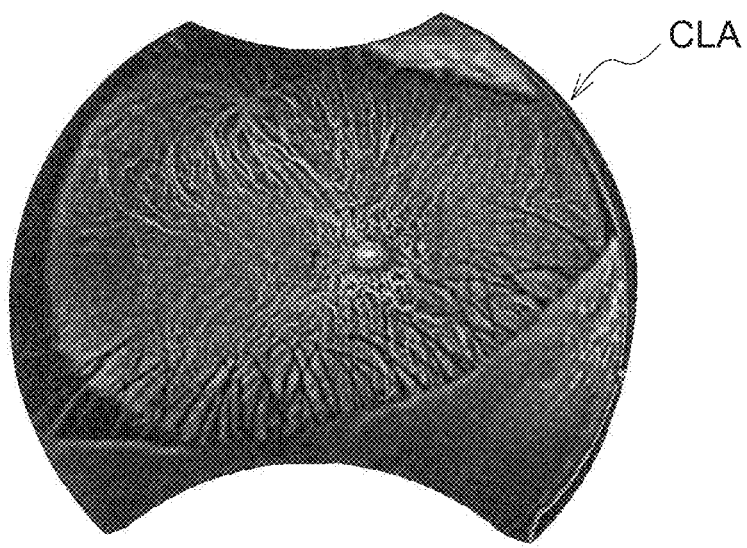
FIG. 13 is a diagram illustrating a choroidal vascular image CLA.

The structure of an eye is one in which a vitreous body is covered by plural layers of differing structure. The plural layers include, from the vitreous body at the extreme inside to the outside, the retina, the choroid, and the sclera. Since red light is of longer wavelength, red light passes through the retina and reaches the choroid. The red fundus image 504RG therefore includes information relating to blood vessels present within the retina (retinal blood vessels) and information relating to blood vessels present within the choroid (choroidal blood vessels). In contrast thereto, due to green light being of shorter wavelength than red light, green light only reaches as far as the retina. The green fundus image 502GG accordingly only includes information relating to the blood vessels present within the retina (retinal blood vessels). This thereby enables a choroidal vascular image CLA to be obtained (see FIG. 13) by extracting the retinal blood vessels from the green fundus image 502GG and removing the retinal blood vessels from the red fundus image 504RG The choroidal vascular image CLA is specifically generated in the following manner.

The image processing control section 206 extracts the retinal blood vessels from the green fundus image 502GG by applying black hat filter processing to the green fundus image 502GG Next, the image processing control section 206 removes the retinal blood vessels from the red fundus image 504RG by performing in-painting processing thereon. Namely, position information for the retinal blood vessels extracted from the green fundus image 502GG is employed when performing processing to infill the positions of the retinal blood vessel structure in the red fundus image 504RG using pixel values the same as those of surrounding pixels. The image processing control section 206 then emphasizes the choroidal blood vessels in the red fundus image 504RG by performing contrast limited adaptive histogram equalization processing on the image data of the red fundus image 504RG from which the retinal blood vessels have been removed. The choroidal vascular image CLA illustrated in FIG. 13 was created in this manner. The created choroidal vascular image CLA is stored in the storage device 254.

In the above example, the choroidal vascular image is generated from the red fundus image 504RG and the green fundus image 502GG However, the image processing control section 206 may generate a choroidal vascular image CLA from the green fundus image 502GG and the UWF-SLO image 508IRG The image processing control section 206 may also generate a choroidal vascular image CLA from the blue fundus image 502BG and one image from out of the red fundus image 504RG or the UWF-SLO image 508IRG Furthermore, a choroidal vascular image CLA may also be generated from the UWF-SLO image (video) 510. As described above, the UWF-SLO image (video) 510 is a video image from the time indocyanine green (ICG) that has been injected into a blood vessel reaches the retina until after the indocyanine green (ICG) has passed through the choroid. The choroidal vascular image CLA may be generated from a video image of a period after the indocyanine green (ICG) has passed through the retina and during which the indocyanine green (ICG) is passing through the choroid.

The diameter of blood vessels in the choroid is generally larger than the diameter of blood vessels in the retina. Specifically, blood vessels of a diameter larger than a specific threshold value are choroidal blood vessels. The choroidal vascular image CLA may accordingly be generated by extracting blood vessels from images in the UWF-SLO image (video) 510 taken when the indocyanine green (ICG) is passing through the blood vessels of the retina and the choroid, and then removing any blood vessels with a diameter smaller than a specific threshold value.

Figure 14:
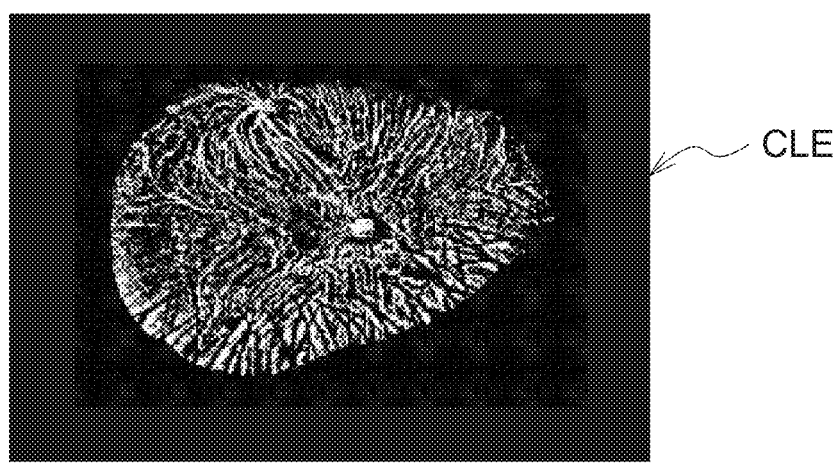
FIG. 14 is a diagram illustrating a choroidal vascular image CLE obtained by processing to crop a choroidal vascular image CLA to a region of the fundus (to remove eyelids etc.)

Since an eyelid or the like may be included in an image of the choroidal blood vessels, the image processing control section 206 performs processing at step 306 to crop the choroidal vascular image CLA to a fundus region (removing eyelids etc.) so as to generate a choroidal vascular image CLE (see FIG. 14). The choroidal vascular image CLA and the choroidal vascular image CLE are thus images in which the choroidal blood vessels have been visualized that were obtained by performing image processing on the fundus images.

At step 308, the image processing control section 206 computes the blood vessel diameter of each choroidal blood vessel in the choroidal vascular image CLE using plural blood vessel center points found along the blood vessel flow direction. Detailed explanation regarding blood vessel diameter computation processing will follow later.

At step 309, the image processing control section 206 creates a database of choroidal blood vessel diameters including at least choroidal blood vessel diameters and pixel coordinates for the blood vessel center points employed in the computation at step 308. This database of choroidal blood vessel diameters is associated with the UWF-SLO fundus images being analyzed, and is stored in the RAM 266 or the storage device 254. Details regarding the structure of the database will be described later.

At step 310, the display control section 204 creates a display image for display on a display screen 800 (see also FIG. 28) to illustrate results of the analysis that employed the blood vessel diameter data computed at step 308. The layout of the display screen will be described in detail later.

At step 312, the processing section 208 transmits display image data for the display image to the image viewer 150 through the communication I/F 258.

Explanation follows regarding processing to compute the choroidal blood vessel diameter, with reference to the flowcharts illustrated in FIG. 7, FIG. 8, FIG. 9, and FIG. 10.

Figure 7:
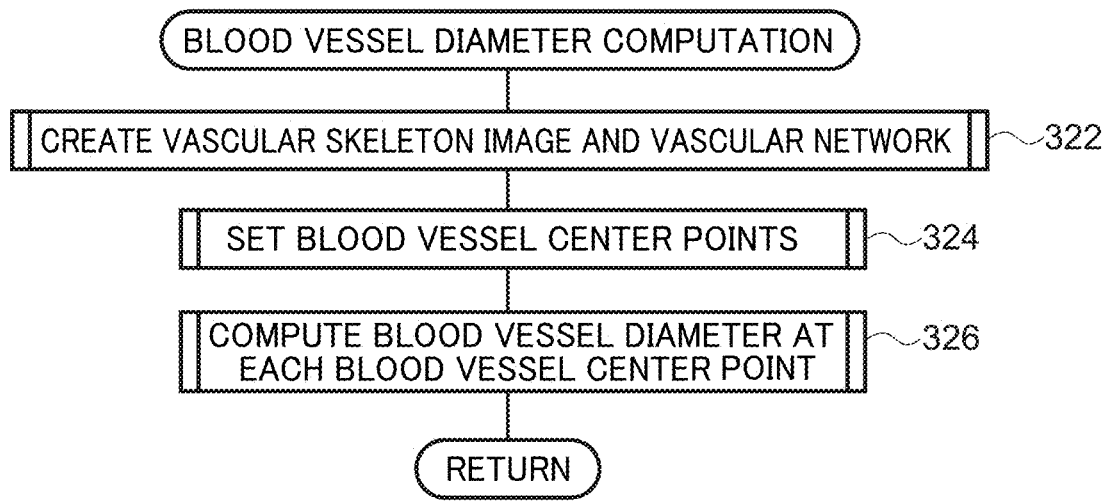
FIG. 7 is a flowchart of blood vessel diameter computation processing performed at step 308 in FIG. 6.
Figure 17:
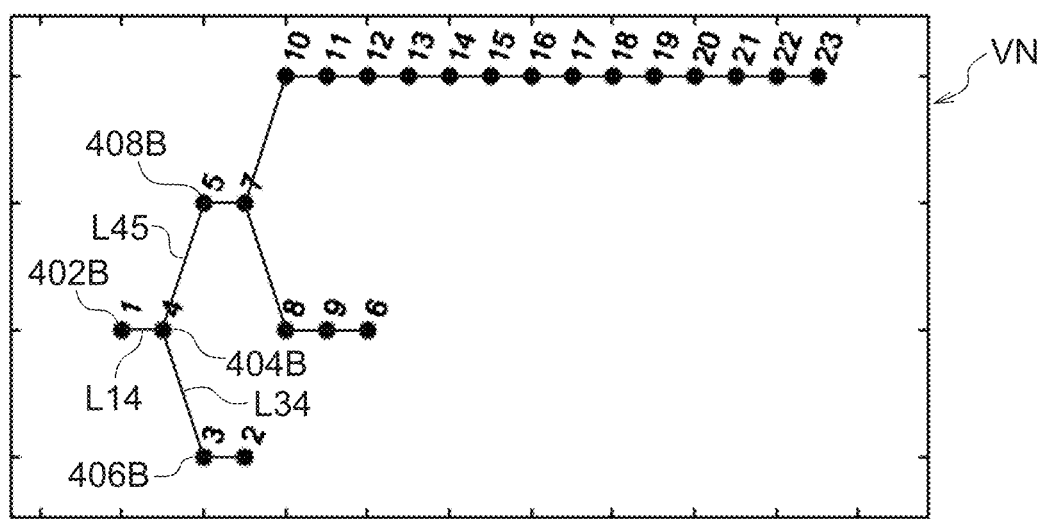
FIG. 17 is a diagram illustrating a vascular network VN.

FIG. 7 is a main flowchart of choroidal blood vessel diameter computation processing. At step 322, the image processing control section 206 creates a vascular skeleton image VS (see FIG. 15) and a vascular network VN (see FIG. 17) as described in detail later. At step 324, the image processing control section 206 sets plural blood vessel center points along the blood vessel flow direction. At step 326 the image processing control section 206 computes the blood vessel diameter at each blood vessel center point, and finally computes the blood vessel diameters of all of the choroidal blood vessels in the choroidal vascular image CLE.

Figure 8:
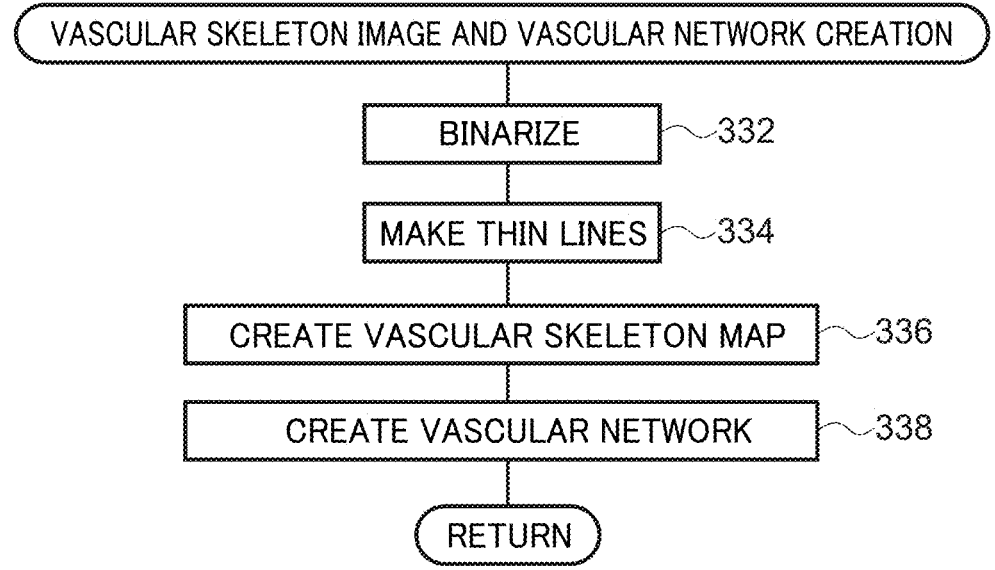
FIG. 8 is a flowchart of processing performed at step 322 in FIG. 7.

FIG. 8 is a flowchart of the processing of step 322 in FIG. 7.

At step 332, the image processing control section 206 creates a non-illustrated choroidal vascular binary image of the choroidal vascular image CLE binarized by referencing the pixel value of each pixel thereof against a specific threshold value. The choroidal vascular binary image is an image in which the choroidal blood vessels are visualized (pixels in blood vessel regions corresponding to choroidal blood vessels are white, and pixels in regions other than choroidal blood vessels are black).

At step 334, the image processing control section 206 finds a line at the center of the each choroidal blood vessel diameter in the choroidal vascular binary image by making lines in the choroidal vascular binary image thinner. The central lines are lines of one pixel width. Namely, the vascular skeleton image VS is generated by performing processing on the binary image to make lines therein thinner so as to convert into a line image configured by lines of one pixel width.

Figure 15:
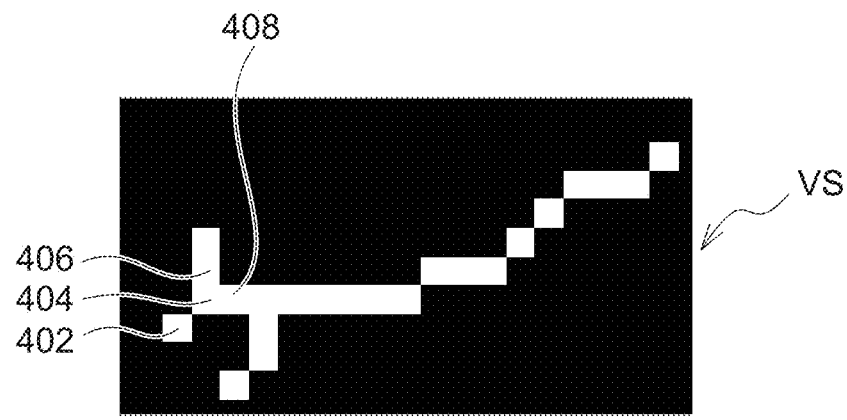
FIG. 15 is a diagram illustrating a vascular skeleton image VS.

FIG. 15 illustrates the vascular skeleton image VS for a single choroidal blood vessel in the choroidal vascular image CLE. As illustrated in FIG. 15, in the vascular skeleton image VS is represented by plural pixels 402, 404, 406, 408, . . . that indicate choroid center lines.

Figure 16:
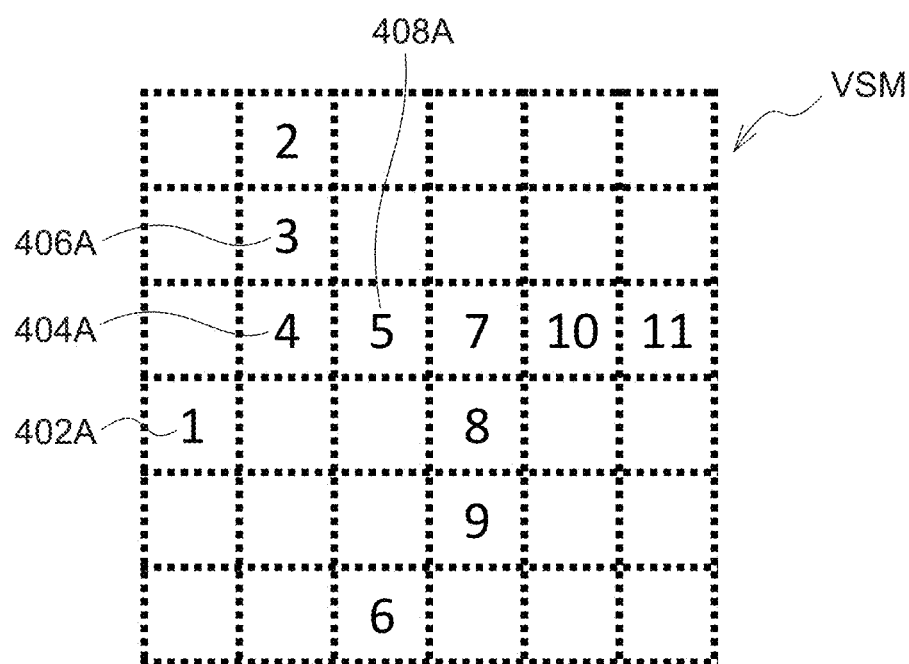
FIG. 16 is a diagram illustrating a vascular skeleton map VSM.

At step 334, as illustrated in FIG. 16, the image processing control section 206 appends pixel numbers to the plural pixels 402, 404, 406, 408, . . . representing the choroidal blood vessel, and creates a vascular skeleton map VSM of pixel positions (or pixel coordinates) associated with the pixel numbers. For example, for the pixel 402 in the vascular skeleton map corresponding to the pixel 402 in the vascular skeleton image VS illustrated in FIG. 15, the pixel number 1 and denoted as pixel number 402A1. For the pixel 404 in the vascular skeleton map VSM corresponding to the pixel 404 in the vascular skeleton image VS, the pixel number 4 is appended as pixel number 404A. The vascular skeleton map VSM illustrated in FIG. 16 is a vascular skeleton map VSM in which a region A of FIG. 15 is displayed. The vascular skeleton map VSM may of course be created for the entire vascular skeleton image VS.

Next, at step 338, the image processing control section 206 creates a vascular network VN from the vascular skeleton map VSM. Note that the vascular network VN employs the pixel numbers from the vascular skeleton map VSM as nodes, and is a graph configured by nodes (points) and edges (lines) in which an edge indicates a connection relationship between pixel numbers.

The image processing control section 206 takes the pixel number 1 of the pixel 402 in the vascular skeleton map VSM to form a node (1) at a specific position (see 402B) within a memory space for creating the vascular network VN.

Next, the image processing control section 206 searches for a pixel appended with a pixel number in the vicinity of the pixel 402 in the vascular skeleton map VSM. Specifically, first the image processing control section 206 searches for a pixel appended with a pixel number at the four neighboring pixels (four pixels heightwise and widthwise, namely at the four pixels above, below, and to the left and right of the pixel 402). In FIG. 16 there are no pixels appended with a number present at the four neighboring pixels of the pixel 402A. Next, the image processing control section 206 searches for pixels appended with pixel numbers at the eight neighboring pixels (eight pixels adjacent heightwise, widthwise, and diagonally, namely the eight pixels arrived at by adding the four pixels diagonally to the left and diagonally to the right to the four pixels above, below, and to the left and right of the pixel 402). In FIG. 16, the pixel number 4 is appended to the pixel 404 present at the diagonal upper right of the pixel 402. The image processing control section 206 accordingly sets the pixel number 4 appended to the pixel 404 as a new node (4) to the pixel number 1 appended to the pixel 402 (see 402B in FIG. 17). The node (1) and the node (4) are connected together by an edge (see FIG. 18). In consideration of blood vessel branching, the processing is ended at the point in time when no pixels appended with pixel numbers are discovered. The vascular network VN is created by performing processing of this nature to the entire vascular skeleton map VSM.

After completing step 338 to create the vascular network VN, the image processing control section 206 ends the subroutine illustrated in FIG. 8 and returns to the main flowchart illustrated in FIG. 7.

FIG. 9A and FIG. 9B are flowcharts illustrating the processing of step 324 in FIG. 7. FIG. 9A is a flowchart illustrating the setting of the blood vessel center points, and FIG. 9B illustrates a search subroutine for the blood vessel center points.

At step 1300, the image processing control section 206 projects the vascular skeleton image VS onto the surface of an eyeball model. The model eyeball surface is a spherical surface corresponding that of an eyeball as reproduced in a memory space of the RAM 266 by the image processing control section 206 based on the eye axial length, age, and the like of the examinee. An inverse stereographic transformation is performed on the vascular skeleton image VS so as to project the vascular skeleton image VS onto the surface of the model eyeball. This approach is adopted since the UWF-SLO image is itself an image produced by stereographically projecting an eyeball onto a two-dimensional plane. Although some distortion arises due to the stereographic transformation at peripheral portions of the UWF-SLO image and the vascular skeleton image VS, the effect of such distortion can be removed by performing inverse stereographic transformation and projection onto the model eyeball surface. Values close to the actual blood vessel diameters can be obtained due to the blood vessel diameters being computed in a state in which such distortion has been removed.

At step 1320, the image processing control section 206 sets a given end point of the vascular skeleton image VS as a current search point. The current search point set at step 1320 is employed as a search start point for the vascular skeleton image NL, and is a start point employed to search the blood vessel center points. To explain the skeleton image illustrated in FIG. 19, an asterisk (*) labeled 460N1 in the vascular skeleton image is set as the current search point.

At step 1340, the image processing control section 206 starts the processing of a subroutine illustrated in FIG. 9B to search blood vessel center points. The subroutine illustrated in FIG. 9B is a subroutine called up recursively at step 1340 in FIG. 9A and at step 1500 in FIG. 9B.

At step 1400, the image processing control section 206 sets the current search point 460N1 as a blood vessel center point.

Figure 18:
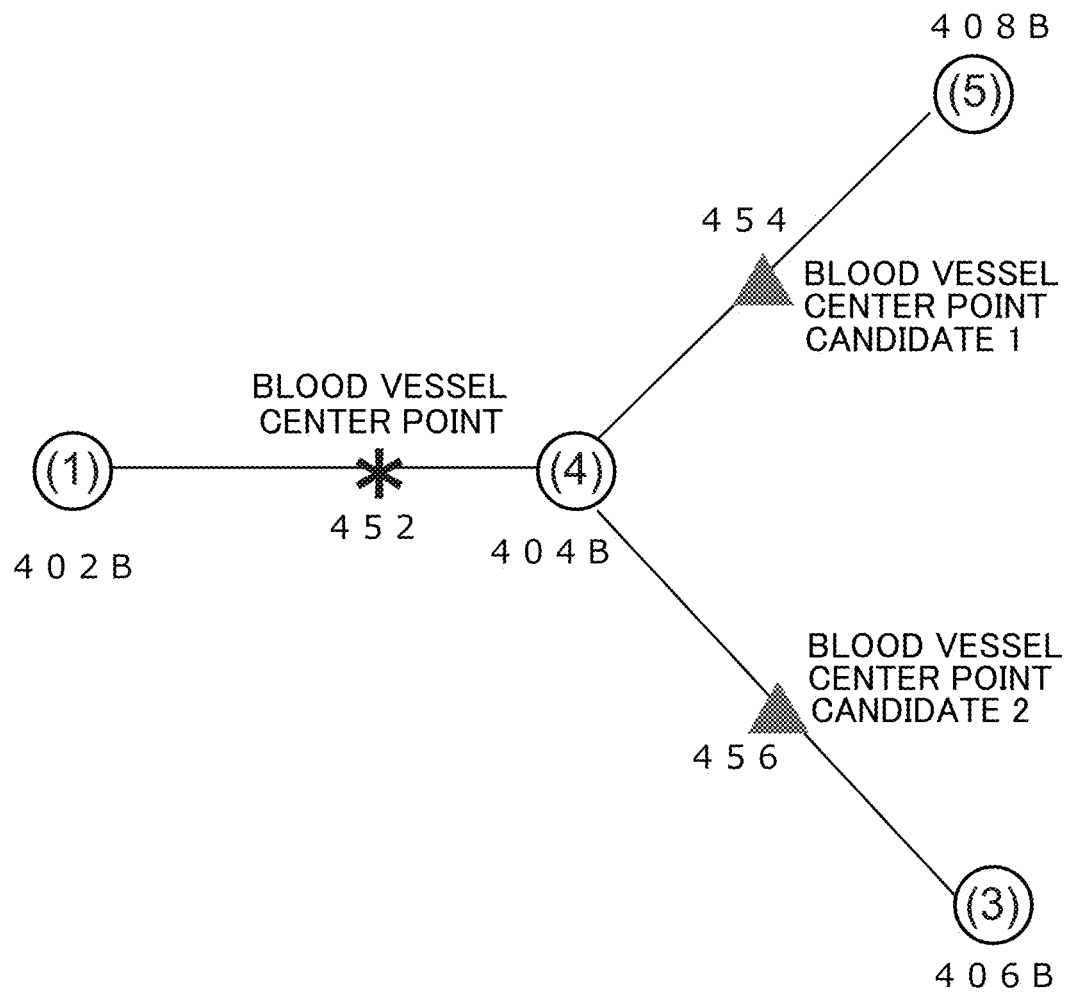
FIG. 18 is a diagram illustrating part of a vascular network VN.

At step 1420, the image processing control section 206 sets a point in the vascular skeleton image VS separated by a fixed distance (for example 20 μm) from the blood vessel center point as a blood vessel center point candidate. The number of "blood vessel center point candidates" is one where there is no branch in the blood vessel within the fixed distance from the blood vessel center point and the blood vessel continues as a single vessel, and two blood vessel center point candidates are set for the respective blood vessels in cases in which the blood vessel branches (the blood vessel branches into a two pronged fork). A blood vessel center point candidate is not, however, set when there is no blood vessel is present at all. FIG. 18 is a diagram schematically illustrating a relationship between a vascular network VN, blood vessel center points, and blood vessel center point candidates. 402B, 404B, 406B and 408B respectively correspond to node (1), node (2), node (3), and node (5) of the vascular network VN. A blood vessel center point 452 has already been set between node (1) and node (4). The blood vessel branches into two at the node (4), such that the next blood vessel center point candidates are set as the blood vessel center point candidate 1, labeled 454, positioned between node (4) and node (5), and blood vessel center point candidate 2, labeled 456, between node (4) and node (3).

At step 1440, the image processing control section 206 decides a blood vessel flow direction as a direction between the blood vessel center point and the blood vessel center point candidate. Spherical surface coordinate data of the blood vessel center point on the model eyeball surface, the blood vessel flow direction, and a unique blood vessel center point number are appended and stored in the RAM 266.

Figure 19:
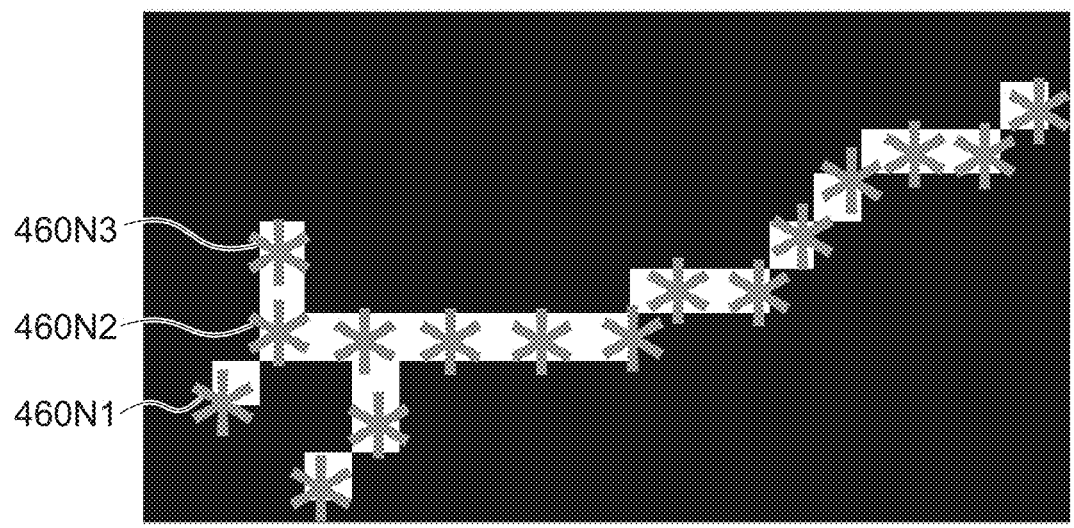
FIG. 19 is a diagram illustrating a vascular skeleton image.

Next, processing proceeds to the processing loop of from step 1460 to step 1500. The number of times this processing loop is executed depends on the number of blood vessel center point candidates set at step 1420. Namely, the processing loop is executed once when the blood vessel does not branch and continues as a single blood vessel, and the processing loop is executed twice when the blood vessel branches (the blood vessel branches into a two pronged fork). In FIG. 19, the point 460N2 is a blood vessel center point candidate.

The image processing control section 206 ends the subroutine illustrated in FIG. 9B without executing the processing loop at step 1460 when there is no blood vessel center point candidate present, and processing transitions to step 1360 of FIG. 9A. At step 1360, the image processing control section 206 stores and retains data for all blood vessel center points already set (data including at least spherical surface coordinate data of the blood vessel center point on the model eyeball surface, a blood vessel flow direction, and a unique blood vessel center point number) in the RAM 266 or in the storage device 254. A configuration may be adopted in which the blood vessel flow direction is set for the immediately preceding blood vessel center point since the blood vessel flow direction cannot be computed for the blood vessel center point positioned at the end of a blood vessel.

Processing proceeds to step 1480 when there is a blood vessel center point candidate present. When there is a blood vessel center point candidate present, at step 1480 the image processing control section 206 sets the blood vessel center point candidate as the current search point.

Processing then proceeds to step 1500, and the image processing control section 206 recursively executes the subroutine illustrated in FIG. 9B. When search processing for blood vessel center points of a blood vessel branch comes to an end at step 1500, the processing loop for the blood vessel branch is ended at step 1520, processing returns to step 1460, and the search processing is repeated for blood vessel center points of another blood vessel branch. In this manner, the presence or absence of blood vessel branches is determined from the vascular network NV, and blood vessel center points can be set for all of the blood vessels within the vascular skeleton image VS by repeating the processing loop.

Next, explanation follows regarding computation of the blood vessel diameter for each blood vessel center point at step 326 in FIG. 7. FIG. 10 is a flowchart of the processing of step 326 in FIG. 7. The processing in FIG. 10 employs data of the blood vessel center points set by the processing illustrated in FIG. 9A and FIG. 9B to compute the blood vessel diameter of the choroidal blood vessels in the choroidal vascular binary image (FIG. 14) projected onto the model eyeball surface at each blood vessel center point.

Specifically, at step 372, the image processing control section 206 reads the data relating to blood vessel center points that was stored at step 1360 in FIG. 9A. One blood vessel center point is selected therein, and the spherical surface coordinate data of the selected blood vessel center point on the model eyeball surface and the blood vessel flow direction are identified.

Figure 20:
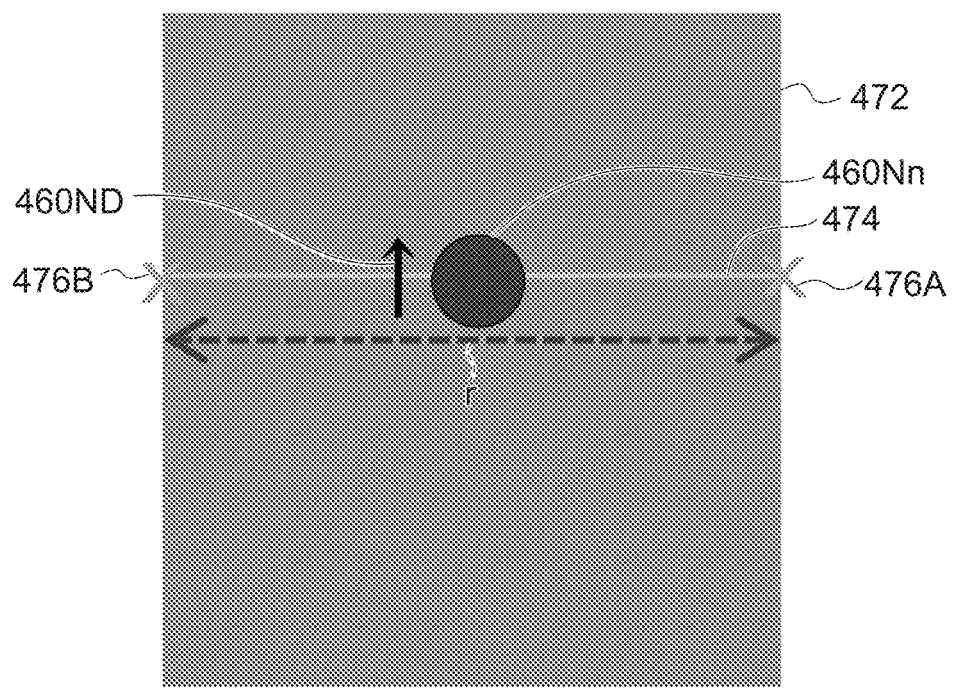
FIG. 20 is a diagram illustrating a blood vessel diameter at a blood vessel center point of a choroidal blood vessel in a choroidal vascular binary image projected onto a model eyeball surface.
Figure 21:
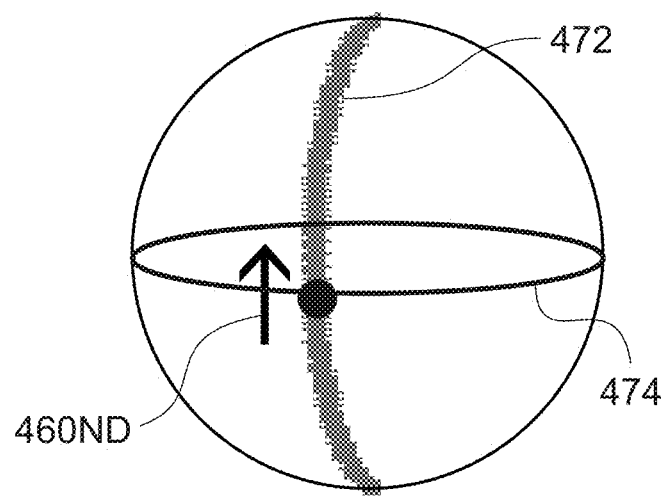
FIG. 21 is a diagram illustrating a great circle.

At step 374, the image processing control section 206 computes a great circle orthogonal to the blood vessel flow direction at the selected blood vessel center point. Specifically, as illustrated in FIG. 20 and FIG. 21, the image processing control section 206 computes, in the choroidal vascular binary image projected onto the above model eyeball surface, a great circle 474 (FIG. 21) orthogonal to the blood vessel flow direction 460ND at the identified blood vessel center point 460Nn. Here, the center of the great circle is the same as the center of the model eyeball.

At step 376, the image processing control section 206 computes the intersections between the great circle 474 and the blood vessel edges. Specifically, as described above, the great circle 474 is positioned in the choroidal vascular binary image projected onto the model eyeball surface with reference to the blood vessel center point 460Nn. The image processing control section 206 computes intersections 476A, 476B between the thus positioned great circle 474 and the blood vessel edges of the choroidal blood vessel in the choroidal vascular binary image on the above model eyeball surface.

At step 378, a distance r between the intersection 476A and the intersection 476B is computed, and this is stored associated with the blood vessel center point in the vascular skeleton image. The distance r is a segment of the great circle 474 and is the shortest distance passing through the blood vessel center point 460Nn on the model eyeball surface. This enables the diameter to be obtained for a blood vessel approximating to the shape of the eyeball.

Figure 22:
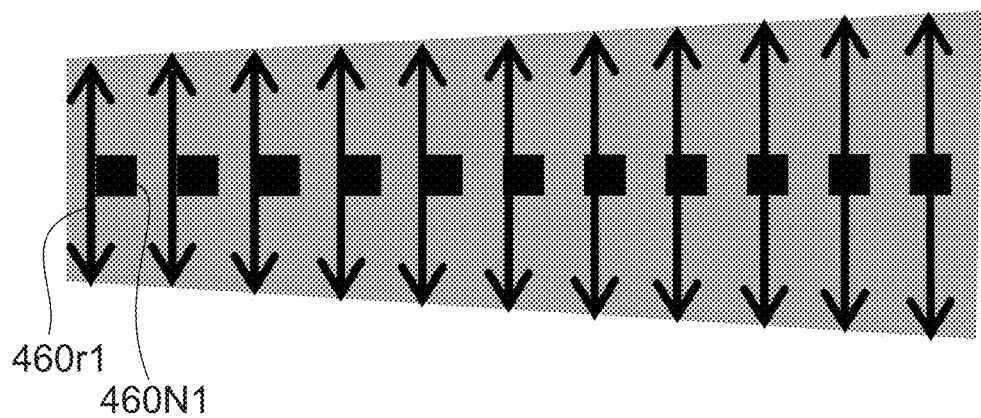
FIG. 22 is a diagram illustrating blood vessel diameters at respective blood vessel center points of a choroidal blood vessel in a choroidal vascular binary image.

In this manner, the processing of FIG. 10 is performed for all of the blood vessel center points in the vascular skeleton image VS. Accordingly, as illustrated in FIG. 22, the blood vessel diameters are computed for each of the blood vessel center points in the choroidal vascular binary image on the model eyeball surface. Note that the blood vessel diameter at each blood vessel center point is associated with the blood vessel center point number, and stored and retained in the RAM 266 or the storage device 254.

The choroidal blood vessel diameter database creation processing performed at step 309 in FIG. 6 is illustrate in the flowchart of FIG. 11. At step 382, the image processing control section 206 reads data relating to retained blood vessel center point number, spherical surface coordinate data on the model eyeball surface, blood vessel flow direction, and blood vessel diameter.

Figure 23:
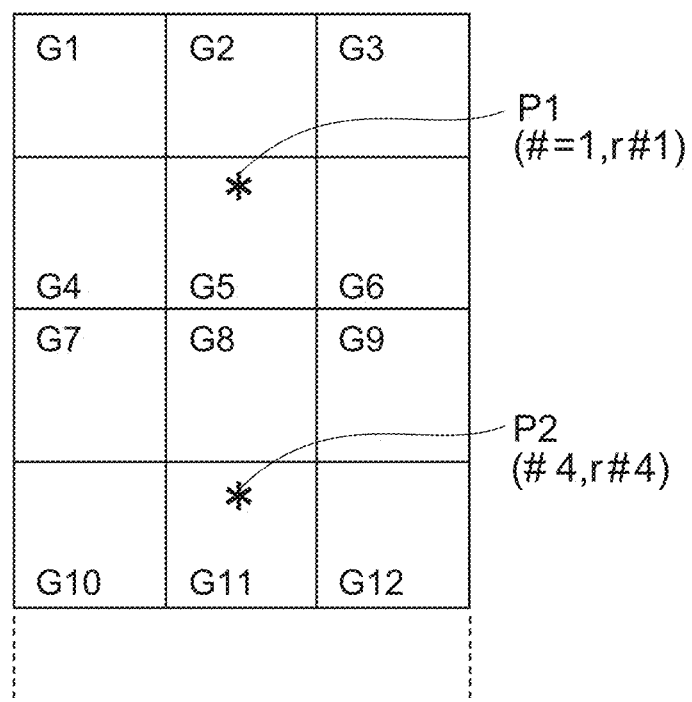
FIG. 23 is a diagram illustrating a relationship between positions P1, P2, . . . and so on corresponding to blood vessel center points and pixels of a choroidal vascular binary image.
Figure 24:
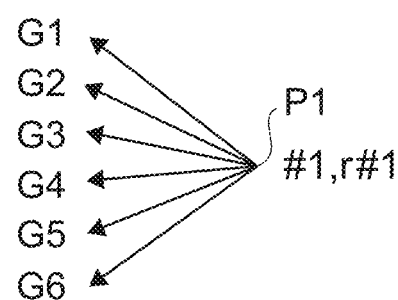
FIG. 24 is a diagram illustrating a manner in which a number and a blood vessel diameter at a position P1 corresponding to a blood vessel center point are associated with pixels G1 to G6 of a choroidal vascular binary image.
Figure 25:
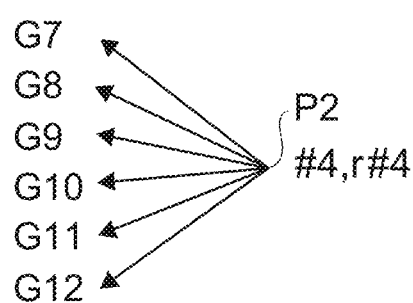
FIG. 25 is a diagram illustrating a manner in which a number and a blood vessel diameter at a position P2 corresponding to a blood vessel center point are associated with pixels G7 to G12 of a choroidal vascular binary image.

At step 385, the image processing control section 206 labels each pixel that represents a blood vessel with a number and a direction of the blood vessel center point closest to this pixel. Specifically, as illustrated in FIG. 23, the image processing control section 206 identifies positions P1, P2, . . . that correspond to blood vessel center points in the choroidal vascular binary image (FIG. 14) (namely, spherical surface coordinate data representing the blood vessel center point on the model eyeball surface are converted into two-dimensional coordinate data representing the blood vessel center point on a two-dimensional image). The image processing control section 206 identifies the closest blood vessel center point for each pixel representing a blood vessel in the choroidal vascular binary image. Each pixel is associated (labeled) with the number and blood vessel diameter of the identified blood vessel center point. More specifically, as illustrated in FIG. 24, the display control section 204 associates a number (#=1) and a blood vessel diameter (r #1) of the blood vessel center point P1 closest to each pixel with the pixels G1 to G6 that represent a blood vessel in the choroidal vascular binary image. Similarly, as illustrated in FIG. 25, the display control section 204 associates a number (#=4) and blood vessel diameter (r #4) of the blood vessel center point P2 closest to each pixel with the pixels G7 to G12 that represent a blood vessel in the choroidal vascular binary image.

At step 386, the image processing control section 206 creates a database of the choroidal blood vessel diameters. FIG. 26 illustrates a database of the choroidal blood vessel diameters. As illustrated in FIG. 26, the choroidal blood vessel diameter database is provided with a storage region 502 to store data numbers of choroidal vascular images. The image processing control section 206 stores in the storage region 502 data numbers M1, M2, . . . and so on to discriminate between the respective choroidal vascular images.

The choroidal blood vessel diameter database is also provided with a storage region 504 to store unique skeleton numbers for blood vessels in the respective vascular skeleton images of the choroidal vascular images discriminated by the choroidal vascular image data numbers. For example, skeleton numbers S1, S2, . . . and so on of the blood vessels in each of the vascular skeleton images of the choroidal vascular image discriminated by the choroidal vascular image data number M1 are associated with the data number M1 and stored in the storage region 504 by the image processing control section 206. Alternatively, a configuration may be adopted in which the vascular network NV is analyzed to discriminate blood vessels which are then applied with skeleton numbers.

The choroidal blood vessel diameter database is also provided with a storage region 506 in which the blood vessel length of each blood vessel is stored. The image processing control section 206 performs the processing of step 1300 in FIG. 9A and also calculates and retains the blood vessel length on the model eyeball surface for each blood vessel when the vascular skeleton image has been pasted onto the model eyeball surface. The calculated blood vessel lengths are then associated with the skeleton number and stored in the storage region 506.

The choroidal blood vessel diameter database is provided with a storage region 508 in which a count of blood vessel center points is stored for each blood vessel. The display control section 204 counts the blood vessel center points set for each vascular skeleton image (FIG. 19) (or vascular network (FIG. 17)), and associates the count with the blood vessel length and stores the associated count in the storage region 508.

The blood vessel diameter database is also provided with a storage region 510 in which numbers to discriminate the respective blood vessel center points in a vascular skeleton image are stored. The image processing control section 206 counts the number of each blood vessel center point presenting in each blood vessel and stores the total count of blood vessel center points in the blood vessels in the storage region 510.

The choroidal blood vessel diameter database is also provided with a storage region 512 in which the coordinates of each blood vessel center point on the SLO image (choroidal vascular image (FIG. 13)) are stored. The image processing control section 206 identifies each blood vessel center point in a vascular skeleton image on the SLO image (choroidal vascular image (FIG. 13)), and associates the coordinates of each identified center point with the blood vessel center points and stores the associations in the storage region 512. Note that a configuration may be adopted in which not only are the coordinates of each blood vessel center point on the UWF-SLO image stored, but coordinates of each blood vessel center point on the choroidal vascular binary image are also stored.

The choroidal blood vessel diameter database is also provided with a storage region 514 in which the coordinates of each pixel in the choroidal vascular binary image that has been appended with a blood vessel center point number are stored. The image processing control section 206 identifies which each pixel in the choroidal vascular binary image has been appended with a blood vessel center point number, and associates the coordinates of each identified pixel on the choroidal vascular binary image associated with the coordinates of the blood vessel center point on the SLO image and stores the associations in the storage region 514. Note that the coordinates of the respective pixels match the coordinates in the SLO image (choroidal vascular image (FIG. 13)).

The choroidal blood vessel diameter database is also provided with a storage region 516 in which the blood vessel flow direction at each blood vessel center point is stored. The image processing control section 206 reads the blood vessel flow direction at the blood vessel center point from the vascular network (FIG. 17), and associates the read blood vessel flow direction at the blood vessel center points that have been appended with the blood vessel center point numbers with the coordinates of each pixel in the choroidal vascular binary image and stores the associations in the storage region 516.

The choroidal blood vessel diameter database is also provided with a storage region 518 in which blood vessel diameters at blood vessel center points are stored. The image processing control section 206 reads the blood vessel diameters for blood vessel center points that have been associated with the blood vessel center points in a vascular skeleton image and stored, and then associates the blood vessel diameters with the blood vessel flow direction and stores the associations in the storage region 518.

Note that the choroidal blood vessel diameter database may be divided into two databases, as illustrated in FIG. 27. A first database is provided with the storage regions 502 to 512 and the storage region 518. A second database is provided with the storage regions 514, 516.

At step 388 in FIG. 11, the image processing control section 206 stores and retains the choroidal blood vessel diameter database created at step 386 in the RAM 266 or the storage device 254 together with the corresponding SLO image.

Explanation follows regarding processing to create display screen data at step 310 in FIG. 6.

Figure 28:
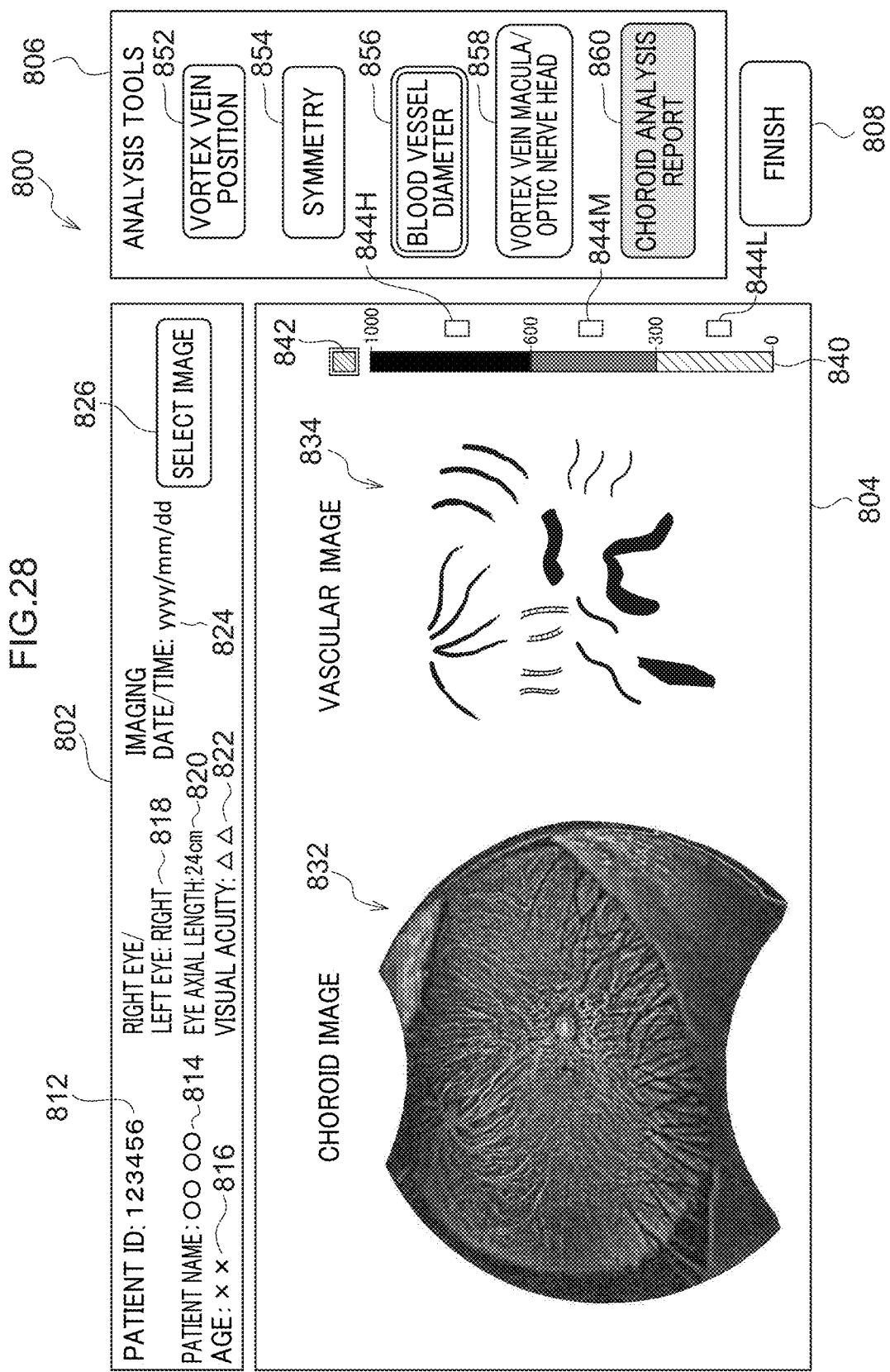
FIG. 28 is a diagram illustrating a display screen 800.

Explanation follows regarding the display screen 800 illustrated in FIG. 28. FIG. 28 illustrates a display screen displayed when a blood vessel diameter icon 856, described later, has been operated. As illustrated in FIG. 28, the display screen 800 includes a personal information display area 802 to display personal information about a patient, an image display area 804, and a choroid analysis tool display area 806.

The personal information display area 802 includes a patient ID display field 812, a patient name display field 814, an age display field 816, a right eye/left eye display field 818, an eye axial length display field 820, a visual acuity display field 822, an imaging date/time display field 824, and a patient selection icon 314. Each of various types of information is respectively displayed in the display fields 812 to 824. Note that a patient list is displayed on a display 172 of the image viewer 150 when the non-illustrated patient selection icon is clicked to prompt the user to select the patient for analysis.

The image display area 804 includes a choroidal vascular image display field 832, a vascular image display field 834, and a diameter range display field 840 to display a range of blood vessel diameters of choroidal blood vessels to be displayed in the vascular image display field 834. The image display field 804 includes icons 844L, 844M, 844H, and an icon 842.

The icon 844L is an icon for the user to instruct choroidal blood vessels with a blood vessel diameter of less than 300 µm to be displayed with a first color in the vascular image display field 834. The icon 344M is an icon for the user to instruct choroidal blood vessels with a blood vessel diameter not less than 300 µm but less than 600 µm to be displayed with a second color different from the first color in the vascular image display field 834. The icon 344H is an icon for the user to instruct choroidal blood vessels with a blood vessel diameter of 600 µm or greater to be displayed with a third color different from both the first color and the second color in the vascular image display field 834.

The icon 842 is an icon for the user to instruct all choroidal blood vessels to be displayed in the vascular image display field 834. When the icon 842 is operated, all choroidal blood vessels are displayed in colors corresponding to their respective blood vessel diameters.

The choroid analysis tool display area 806 is a area to display various icons to select plural choroid analysis. A vortex vein position icon 852, a symmetry icon 854, a blood vessel diameter icon 856, a vortex vein-macula/optic nerve head icon 858, and a choroid analysis report icon 860 are provided to the choroid analysis tool display area 806. The vortex vein position icon 852 is used to instruct the position of the vortex veins to be displayed. The symmetry icon 854 is used to instruct symmetry analysis points to be displayed. The blood vessel diameter icon 856 is used to instruct analysis results relating to the diameter of choroidal blood vessel to be displayed. The vortex vein-macula/optic nerve head icon 858 is used to instruct analysis results of analyzed positions between the vortex veins, the macula, and the optic nerve head to be displayed. The choroid analysis report icon 860 is used to instruct a choroid analysis report to be displayed.

Figure 29:
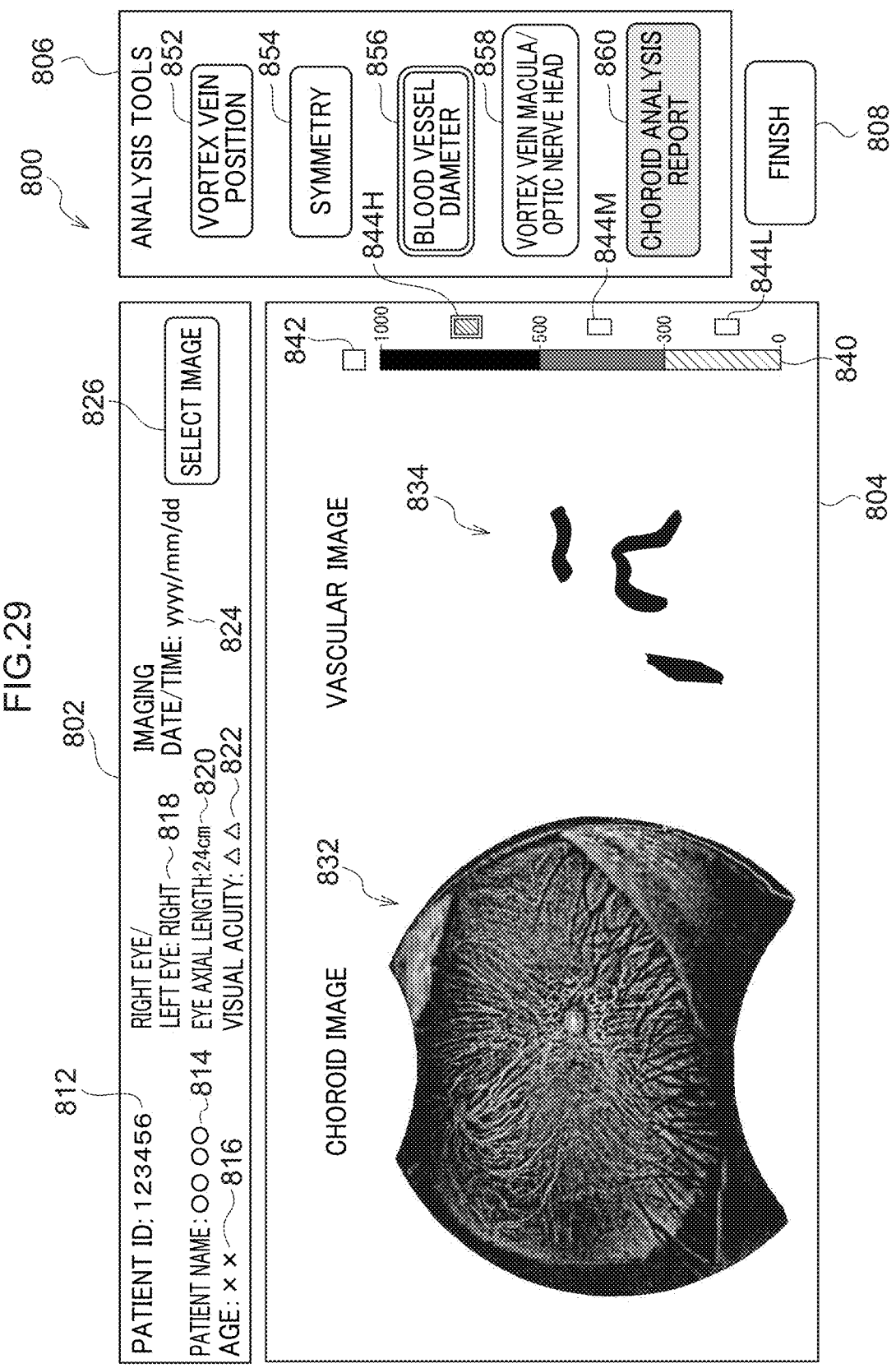
FIG. 29 is a diagram illustrating a display state of choroidal blood vessels having a blood vessel diameter of 600 μm or greater in a vascular image display field 834 when an icon 844H has been operated.

FIG. 29 illustrates a display state of choroidal blood vessels having a blood vessel diameter of 600 µm or greater in the vascular image display field 834 when the icon 844H is operated. Pixels corresponding to blood vessels of a diameter of 600 µm or greater are extracted from the storage region 518 of the choroidal blood vessel diameter database, and the extracted pixels are displayed with the first color in the vascular image display field 834. Similarly, when the icon 844M has been operated, pixels corresponding to blood vessel diameters not less than 300 µm but less than 600 µm are displayed with the second color. When the icon 844L is operated, pixels corresponding to blood vessel diameters of less than 300 µm are displayed with the third color.

Figure 30:
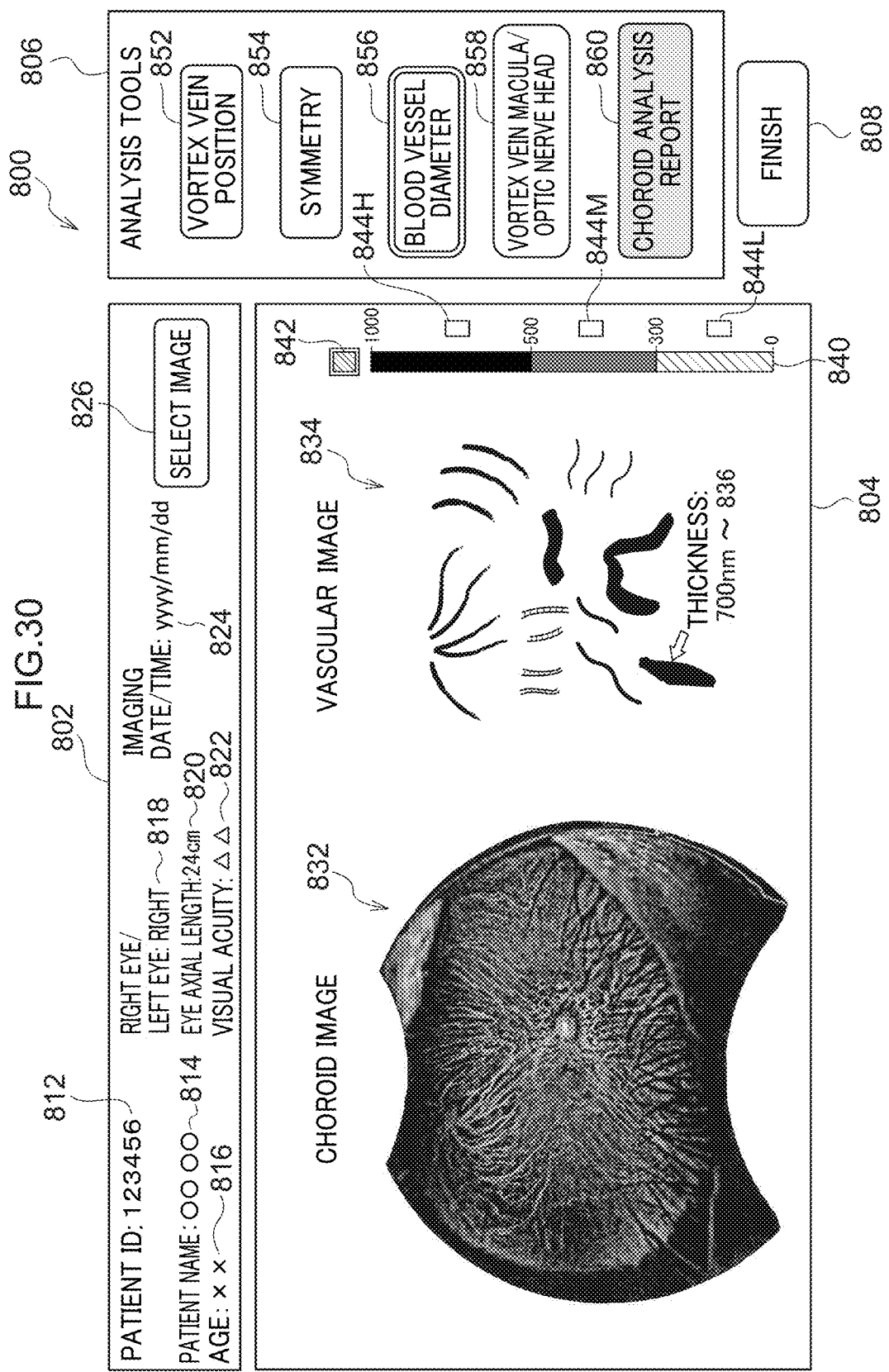
FIG. 30 is a diagram illustrating a display state of a blood vessel diameter of a choroidal blood vessel pointed to by a cursor.

FIG. 30 illustrates a display state of the blood vessel diameter of a choroidal blood vessel pointed to by a cursor. When the user indicates a choroidal blood vessel displayed in the vascular image display field 384 by operating a cursor or the like, the pixel at the cursor position is identified, and the vascular skeleton number to which the identified pixel belongs is identified from the storage region 504. The blood vessel diameters at the blood vessel center points corresponding to this vascular skeleton number are read from the storage region 518, an average value of the read blood vessel diameters is calculated, and this average value is displayed in a display field 836.

Alternatively, a blood vessel diameter associated with the pixel indicated by the cursor may be read from the storage region 518 and displayed as the blood vessel diameter at the indicated blood vessel position. Note that when the cursor has been positioned in a region other than at a choroidal blood vessel, no blood vessel diameter data exists for the pixel where the cursor is positioned, and so a blood vessel diameter is not displayed. Namely, the blood vessel diameter is displayed only when the cursor points to a pixel in a choroidal blood vessel region.

Figure 31:
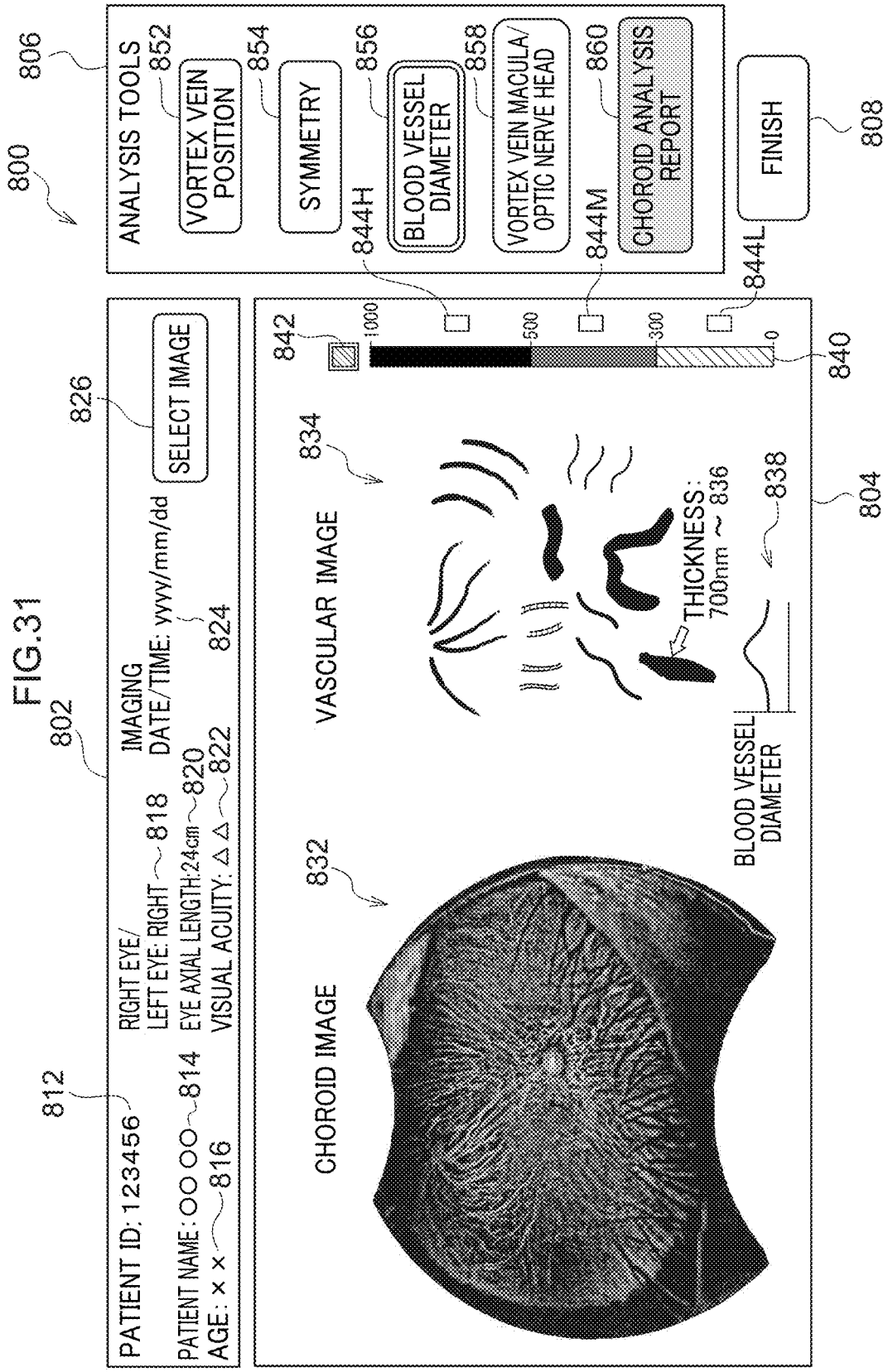
FIG. 31 is a diagram illustrating a display state of a graph 838 representing a pattern of blood vessel diameters of an indicated choroidal blood vessel.

FIG. 31 illustrates a display state of a pattern of blood vessel diameters of an indicated choroidal blood vessel displayed as a graph 838. When the cursor is positioned at a choroidal blood vessel and then clicked, the blood vessel center points corresponding to the relevant vascular skeleton number are read from the storage region 510, and the blood vessel diameters of the blood vessel center points are read from the storage region 518. Blood vessel diameters corresponding to the each blood vessel center point are displayed on the graph 838 with the blood vessel center points on the x axis and the blood vessel diameter on the y axis. The user is thereby able to directly ascertain the blood vessel diameters of curved or meandering blood vessels by using the graph 838.

Figure 32:
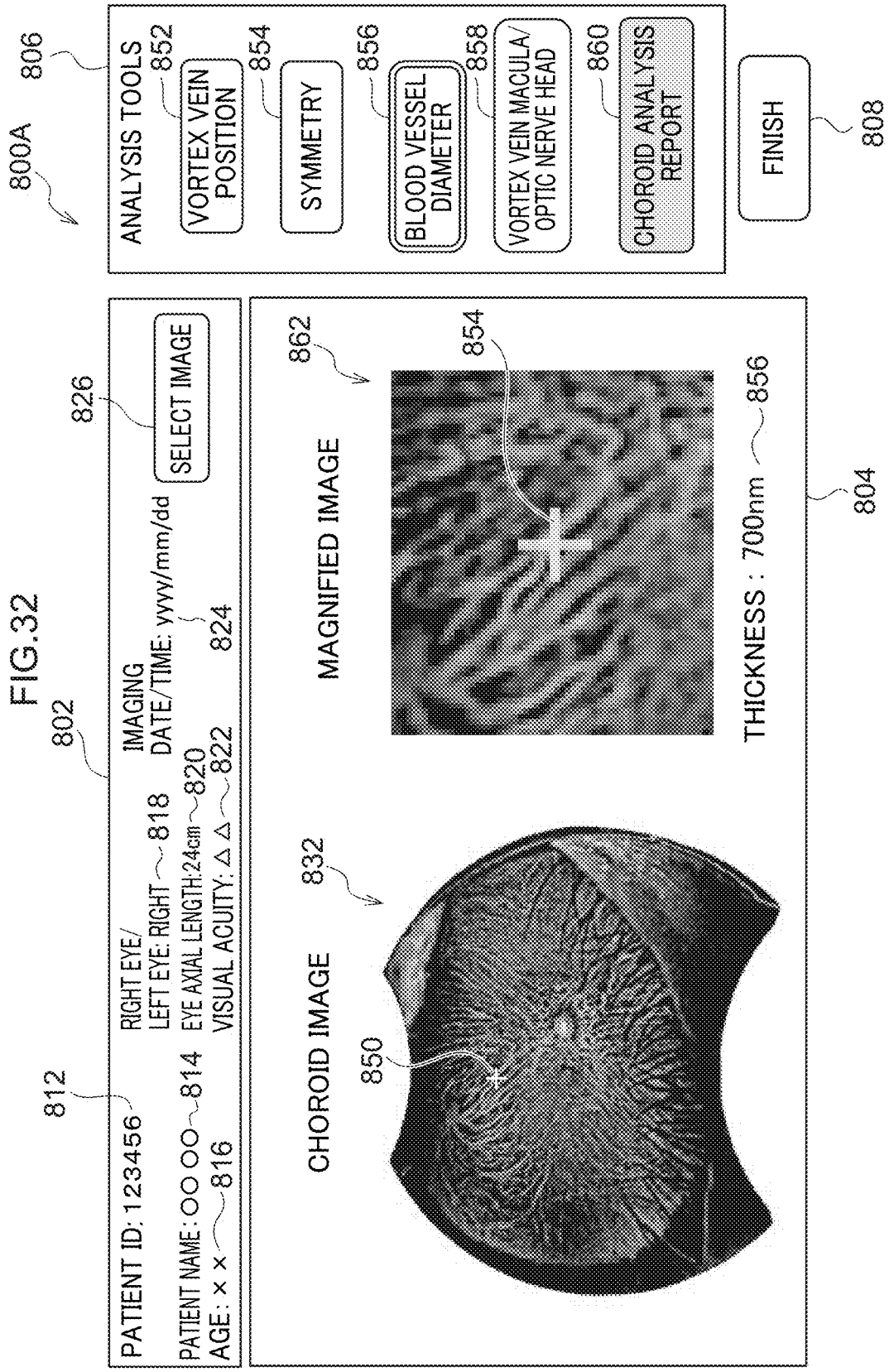
FIG. 32 is a diagram illustrating a second display screen 800A.

FIG. 32 illustrates a second display screen 800A. As illustrated in FIG. 32, an image display area 804 of the display screen 800A includes a choroidal vascular image display field 832 to display a choroidal vascular image, and a magnified image display field 862 to display a magnified image of a specific region including a position indicated in the choroidal vascular image. As illustrated in FIG. 32, the magnified image magnifying the specific region in the choroidal image centered on the position of a cursor or the like is displayed in the magnified image display field 862 when the user operates the cursor to position the cursor (crosshair mark) at a desired point in the choroidal image. Moreover, the pixel where the cursor is positioned is extracted from the storage region 514, and the blood vessel diameter corresponding to the extracted pixel is read from the storage region 518 and is displayed as a numerical value in the magnified image display field 862. Note that when the cursor is positioned in a region other than that of a choroidal blood vessel, no blood vessel diameter data exists for the pixel where the cursor is positioned, and so blood vessel diameter is not displayed. Namely, the blood vessel diameter is displayed only when the cursor points at a pixel in a choroidal blood vessel region.

In the present exemplary embodiment described above, plural blood vessel center points of a choroidal blood vessel are identified, and the respective blood vessel diameters are computed for each of the plural identified blood vessel center points, thereby enabling the choroidal blood vessel diameters to be accurately computed. Moreover, since the blood vessel diameters are computed using an image obtained by projecting the choroidal vascular image onto the model eyeball surface in order to compute the blood vessel diameter, blood vessel diameters that are those of the actual fundus can be obtained. Moreover, various graphical user interfaces (GUI) to assist the user with diagnosis are enabled by creating the choroid database in which the computed blood vessel diameters are associated with the pixels etc. of blood vessel portions.

Second Exemplary Embodiment

Explanation follows regarding a second exemplary embodiment. Since the configuration of the second exemplary embodiment is similar to the configuration of the first exemplary embodiment, explanation thereof is omitted. Since operation of the second exemplary embodiment is largely similar to operation of the first exemplary embodiment, the following explanation mainly concerns elements that differ therefrom.

Figure 33:
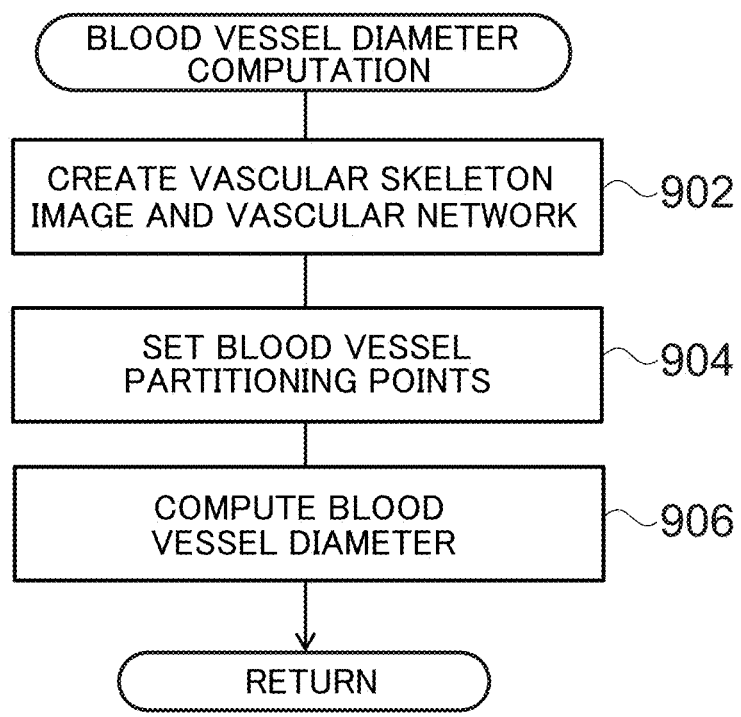
FIG. 33 is a flowchart of blood vessel diameter computation processing performed at step 308 in FIG. 6 in a second exemplary embodiment.
Figure 34:
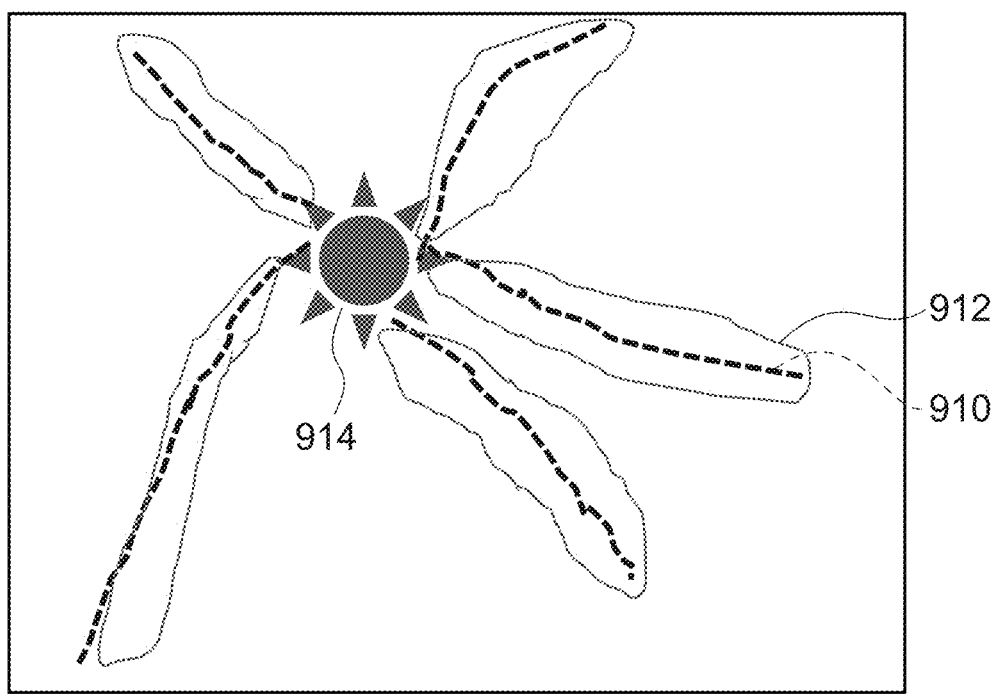
FIG. 34 is a diagram illustrating a range of pixels of a blood vessel region and a vascular skeleton image 910 of a choroidal blood vessel 912.

FIG. 33 is a flowchart of blood vessel diameter computation processing at step 308 in FIG. 6 in the second exemplary embodiment. At step 902 in FIG. 33, processing is executed similar to that of step 322 in FIG. 7. Namely, choroidal blood vessels included in the choroidal vascular binary image (FIG. 34) are identified, and a vascular skeleton image VS and a vascular network VN are created for choroidal blood vessels 912. In FIG. 34, 912 indicates the range of pixels in a blood vessel region, and 910 is a schematic representation of a skeleton image as indicated by dashed lines. 914 indicates a vortex vein position marker 914 indicating the position of a vortex vein.

Figure 35:
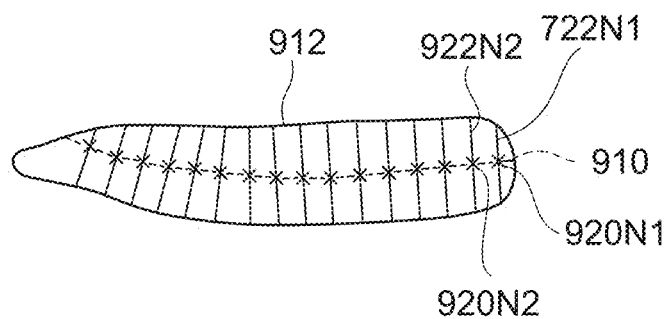
FIG. 35 is a diagram illustrating a choroidal blood vessel 912 partitioned into plural partitioned regions.

As illustrated in FIG. 35, at step 904 the image processing control section 206 sets blood vessel center points 920N1, 920N2, . . . and so on as blood vessel partitioning points to partition the choroidal blood vessel 912 into plural partitioned regions.

At step 906, the image processing control section 206 computes the blood vessel diameters of each choroidal blood vessel in the choroidal vascular binary image (FIG. 34). In the second exemplary embodiment, the image processing control section 206 finds an average of the blood vessel diameters in each of the plural partitioned regions of the choroidal blood vessel 912 in order to find the blood vessel diameter of the choroidal blood vessel. The image processing control section 206 finds the blood vessel diameter of each of the plural partitioned regions of the choroidal blood vessel 912 by dividing the area of each partitioned region by the length of that partitioned region in the blood vessel flow direction.

Specifically, as illustrated in FIG. 35, partitioning lines 922N1, 922N2, . . . and so on are set at the respective blood vessel center points 920N1, 920N2, . . . and so on so as to run in directions perpendicular to the blood vessel flow direction at the blood vessel center points 920N1, 920N2, . . . and so on in respective choroidal blood vessel regions of the choroidal vascular binary image.

Figure 36:
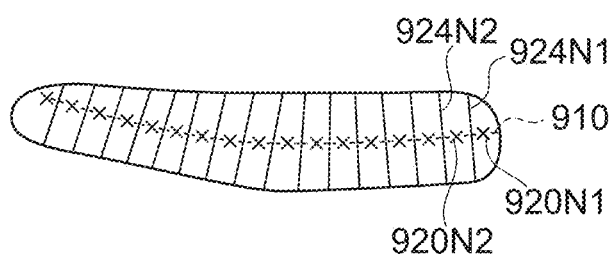
FIG. 36 is a diagram illustrating a choroidal blood vessel 912 partitioned into plural other partitioned regions.

Alternatively, as illustrated in FIG. 36, the partitioning lines 920N1, 920N2, . . . and so on may be set at the centers between adjacent pairs of the blood vessel center points 920N1, 920N2, . . . and so on so as to run in directions perpendicular to the blood vessel flow direction at the blood vessel center points 920N1, 920N2, . . . and so on in the respective choroidal blood vessel regions of the choroidal vascular binary image.

Figure 37:
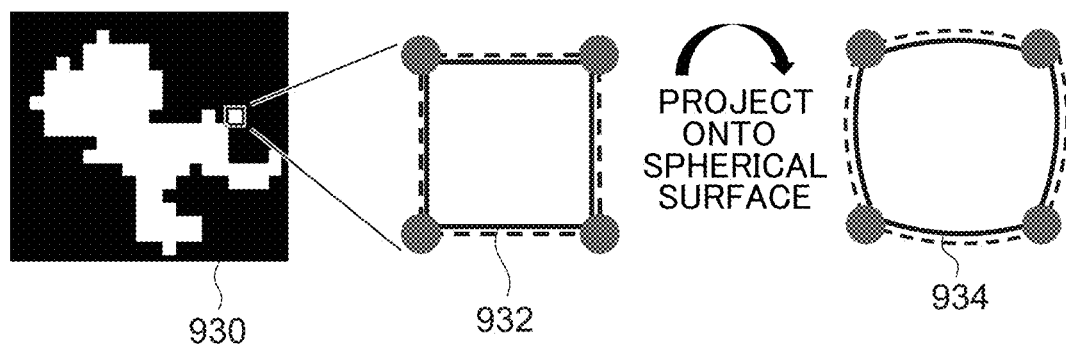
FIG. 37 is a diagram to explain how the area on a model eyeball surface is found for each pixel in a partitioned region of a choroidal blood vessel 912.

The image processing control section 206 extracts an image portion 9301 (FIG. 37) of a partitioned region delineated by the partitioning lines 922N1, 922N2. The image processing control section 206 projects each pixel 932 of each partitioned region image portion 930 onto the model eyeball surface. The image processing control section 206 finds the area of a region 934 obtained by projecting each pixel of the partitioned region image portion 930 onto the model eyeball surface, and calculates the total area of all the pixels in the partitioned region.

The image processing control section 206 calculates the distance on the model eyeball surface between blood vessel center points of the vascular skeleton image 910. The image processing control section 206 computes the blood vessel diameter of the partitioned region between the blood vessel center points by dividing the area of the partitioned region by the distance between blood vessel center points on the model eyeball surface. The image processing control section 206 then finds an average of the blood vessel diameters across all of the partitioned regions of the choroidal blood vessel. The blood vessel diameter of the relevant choroidal blood vessel is computed in this manner.

Explanation follows regarding various modified examples of the technology disclosed herein.

First Modified Example

Although in the exemplary embodiments described above the management server 140 executes the image processing program illustrated in FIG. 6, the technology disclosed herein is not limited thereto. A configuration may be adopted in which the image viewer 150 transmits an image processing command to the management server 140, with the management server 140 executing the image processing program of FIG. 6 in response to this command.

Second Modified Example

In the exemplary embodiments described above, explanation has been given regarding examples in which a fundus image having an internal illumination angle of approximately 200° is acquired by the ophthalmic device 110. The technology disclosed herein is not limited thereto, and the technology disclosed herein may also be applied in a configuration in which a fundus image having an internal illumination angle of 100° or less is captured by an ophthalmic device, or in a configuration in which a montage image synthesized from plural fundus images is employed.

Third Modified Example

Although in the exemplary embodiments described above the fundus image employed is captured by the ophthalmic device 110 provided with an SLO imaging unit, the technology disclosed herein may also be applied to a configuration in which a fundus image captured by a fundus camera capable of imaging choroidal blood vessels, or to an image obtained by OCT angiography is employed.

Fourth Modified Example

In the exemplary embodiments described above, the management server 140 executes the image processing program. The technology disclosed herein is not limited thereto. For example, the ophthalmic device 110 or the image viewer 150 may execute the image processing program.

Fifth Modified Example

Although explanation has been given in the exemplary embodiments described above regarding examples in which the ophthalmic system 100 is provided with the ophthalmic device 110, the eye axial length measurement device 120, the management server 140, and the image viewer 150, the technology disclosed herein is not limited thereto. For example, as a first example, a configuration may be adopted in which the eye axial length measurement device 120 is omitted and the ophthalmic device 110 further includes the functionality of the eye axial length measurement device 120. Alternatively, as a second example, a configuration may be adopted in which the ophthalmic device 110 further includes the functionality of at least one out of the management server 140 or the image viewer 150. For example, the management server 140 may be omitted in cases in which the ophthalmic device 110 includes the functionality of the management server 140. In such cases, the image processing program is executed by the ophthalmic device 110 or the image viewer 150. Alternatively, the image viewer 150 may be omitted in cases in which the ophthalmic device 110 includes the functionality of the image viewer 150. As a third example, a configuration may be adopted in which the management server 140 is omitted, and the image viewer 150 executes the functionality of the management server 140.

Other Modified Examples

The data processing as explained in the exemplary embodiments described above are merely examples thereof. Obviously, unnecessary steps may be omitted, new steps may be added, or the processing sequence may be rearranged within a range not departing from the spirit of the present disclosure.

Although explanation has been given in the exemplary embodiments described above regarding an example in which a computer is employed to implement data processing using a software configuration, the technology disclosed herein is not limited thereto. For example, instead of a software configuration employing a computer, the data processing may be executed solely by a hardware configuration such as a field programmable gate array (FPGA) or an application specific integrated circuit (ASIC). Alternatively, a configuration may be adopted in which some processing out of the data processing is executed by a software configuration, and the remaining processing is executed by a hardware configuration.

Supplements

The following supplements are proposed based on the content described above.

Supplement 1

A data structure for data employed by a computer equipped with a control section and a storage medium and stored on the storage medium, wherein:

the control section reads the data from the storage medium and employs the data in processing to compute a blood vessel diameter of a choroidal blood vessel; and the data includes data regarding plural blood vessel center points of the choroidal blood vessel; and data regarding a blood vessel diameter at each of the blood vessel center points.

Supplement 2

A data structure for data employed by a computer equipped with a control section and a storage medium and stored on the storage medium, wherein:

the control section reads the data from the storage medium and employs the data in processing to compute a blood vessel diameter of each of plural choroidal blood vessels; and the data includes data regarding plural blood vessel center points of each of the choroidal blood vessels associated with each of the plural choroidal blood vessels; and data regarding a blood vessel diameter at each of the blood vessel center points associated with each of the plural choroidal blood vessels.

Supplement 3

A data structure for data employed by a computer equipped with a display section, a control section and a storage medium and stored on the storage medium, wherein:

the control section reads the data from the storage medium and employs the data in processing to display on the display section a choroidal vascular image and a blood vessel diameter at an indicated location on a choroidal blood vessel in the choroidal vascular image; and the data includes data regarding each pixel of the choroidal vascular image;

data regarding plural blood vessel center points of the choroidal blood vessel in the choroidal vascular image; and data regarding a blood vessel diameter at each of the blood vessel center points.

Supplement 4

A storage medium stored with data regarding plural blood vessel center points on a choroidal blood vessel stored in association with data regarding a blood vessel diameter at each of the blood vessel center points.

Supplement 5

A storage medium stored with data regarding plural blood vessel center points on each choroidal blood vessel stored in association with plural respective choroidal blood vessels and with data regarding a blood vessel diameter at each of the blood vessel center points stored in association with the plural respective choroidal blood vessels.

Supplement 6

A storage medium stored with mutually associated data including data regarding each pixel of a choroidal vascular image, data regarding plural blood vessel center points of the choroidal blood vessel in the choroidal vascular image, and data regarding a blood vessel diameter at each of the blood vessel center points.

Supplement 7

A blood vessel diameter computation device including:
a storage medium stored with data regarding plural blood vessel center points of a choroidal blood vessel stored in association with data regarding a blood vessel diameter at each of the blood vessel center points; and
a processor configured to compute a blood vessel diameter of the choroidal blood vessel based on the data stored on the storage medium of the data regarding plural blood vessel center points of the choroidal blood vessel and the data regarding a blood vessel diameter at each of the blood vessel center points.

Supplement 8

A blood vessel diameter computation device including:
a storage medium stored with data regarding plural blood vessel center points on each choroidal blood vessel stored in association with plural respective choroidal blood vessels and data regarding a blood vessel diameter at each of the blood vessel center points stored in association with the plural respective choroidal blood vessels; and
a processor configured to compute a blood vessel diameter of each of the plural choroidal blood vessels based on the data regarding plural blood vessel center points of the respective choroidal blood vessels stored on the storage medium in association with the plural respective choroidal blood vessels and based on the data regarding the blood vessel diameter at each of the blood vessel center points.

Supplement 9

A blood vessel diameter computation device including:
a storage medium stored with mutually associated data including data regarding each pixel of a choroidal vascular image, data regarding plural blood vessel center points of the choroidal blood vessel in the choroidal vascular image, and data regarding a blood vessel diameter at each of the blood vessel center points; and
a processor configured to compute a blood vessel diameter at an indicated location on the choroidal blood vessel in the choroidal vascular image being displayed on a display section based on stored in association with each other on the storage medium including data regarding each pixel of the choroidal vascular image, data regarding plural blood vessel center points of the choroidal blood vessel in the choroidal vascular image, and data regarding a blood vessel diameter at each of the blood vessel center points.

What is claimed is:

1. An image processing method executed by a processor, the image processing method comprising:
acquiring a choroidal vascular image;
acquiring data in which a plurality of blood vessel center points of a choroidal blood vessel comprising a blood vessel in a fundus identified along a flow direction of the choroidal blood vessel in the choroidal vascular image, blood vessel diameters computed at the respective blood vessel center points, and respective pixels on the choroidal blood vessel associated with at least one of the blood vessel center points based on distance from the blood vessel center points of the choroidal blood vessel are included;
displaying a representation of the choroidal blood vessel comprising the blood vessel in the fundus so as to change pixel values of the pixels on the choroidal blood vessel according to sizes of the blood vessel diameters based on the acquired data, and
when a specific value of blood vessel diameter is designated, displaying only pixels on the choroidal blood vessel associated with the blood vessel center points greater than or equal to the designated value of blood vessel diameter, from among the pixels on the choroidal blood vessel.

2. The image processing method of claim 1, further comprising, when a single specific pixel on the choroidal blood vessel is designated, displaying a blood vessel diameter associated with the pixel on the choroidal blood vessel as a numeric value at the blood vessel center points.

3. The image processing method of claim 1, further comprising, when a single specific pixel on the choroidal blood vessel is designated, displaying an average of a plurality of blood vessel diameters associated with each of a plurality of blood vessel center points in the blood vessel to which the pixel on the choroidal blood vessel belongs, as a numerical value.

4. The image processing method of claim 1, wherein the choroidal vascular image is the choroidal vascular image of a fundus.

5. The image processing method of claim 1, further comprising:
displaying only choroidal vessels of a selected vessel diameter.

6. The image processing method of claim 1, further comprising:
displaying the representation of the choroidal blood vessel comprising the blood vessel in the fundus in different colors according to the sizes of the blood vessel diameters based on the acquired data.

7. An image processing device, comprising memory and a processor coupled to the memory, wherein the processor is configured to:
acquire a choroidal vascular image;
acquire data in which a plurality of blood vessel center points of a choroidal blood vessel comprising a blood vessel in a fundus identified along a flow direction of the choroidal blood vessel in the choroidal vascular image, blood vessel diameters computed at the respective blood vessel center points, and respective pixels on the choroidal blood vessel associated with at least one of the blood vessel center points based on distance from the blood vessel center points of the choroidal blood vessel are included;
display a representation of the choroidal blood vessel comprising the blood vessel in the fundus so as to change pixel values of the pixels on the choroidal blood vessel according to sizes of the blood vessel diameters based on the acquired data, and
when a specific value of blood vessel diameter is designated, displaying only pixels on the choroidal blood vessel associated with the blood vessel center points greater than or equal to the designated value of blood vessel diameter, from among the pixels on the choroidal blood vessel.

8. A non-transitory storage medium storing an image processing program executable by a computer to perform processing, the processing comprising:
acquiring a choroidal vascular image;
acquiring data in which a plurality of blood vessel center points of a choroidal blood vessel comprising a blood vessel in a fundus identified along a flow direction of the choroidal blood vessel in the choroidal vascular image, blood vessel diameters computed at the respective blood vessel center points, and respective pixels on the choroidal blood vessel associated with at least one of the blood vessel center points based on distance from the blood vessel center points of the choroidal blood vessel are included;

displaying a representation of the choroidal blood vessel comprising the blood vessel in the fundus so as to change pixel values of the pixels on the choroidal blood vessel according to sizes of the blood vessel diameters based on the acquired data, and when a specific value of blood vessel diameter is designated, displaying only pixels on the choroidal blood vessel associated with the blood vessel center points greater than or equal to the designated value of blood vessel diameter, from among the pixels on the choroidal blood vessel.

* * * * *